United States Patent [19]

Huang et al.

[11] Patent Number: 5,041,453

[45] Date of Patent: Aug. 20, 1991

[54] QUINOLINYL-BENZOHETEROBICYCLIC DERIVATIVES AS ANTAGONISTS OF LEUKOTRIENE D4

[75] Inventors: Fu-Chih Huang, Gwynedd; Keith S. Learn, Upper Darby; Ashvin V. Gavai, Lancaster, all of Pa.

[73] Assignee: Rhone-Poulenc Rorer Pharmaceuticals Inc., Ft. Washington, Pa.

[21] Appl. No.: 532,464

[22] Filed: May 30, 1990

[51] Int. Cl.[5] .................. C07D 401/10; C07D 403/10; A61K 31/47
[52] U.S. Cl. ..................... 514/314; 546/172; 546/174; 546/175; 546/176
[58] Field of Search ............... 546/174, 314, 172, 175, 546/176

[56] References Cited

U.S. PATENT DOCUMENTS

| | | | |
|---|---|---|---|
| 4,186,201 | 1/1980 | Erickson | 514/314 |
| 4,851,409 | 7/1989 | Young et al. | 514/314 |
| 4,920,131 | 4/1990 | Huang et al. | 514/314 |
| 4,946,855 | 8/1990 | Yoshiuaga et al. | 514/314 |

FOREIGN PATENT DOCUMENTS 0387610 9/1990 European Pat. Off. ............ 546/172

*Primary Examiner*—David B. Springer
*Attorney, Agent, or Firm*—James A. Nicholson; Imre (Jim) Balogh; Martin F. Savitzky

[57] ABSTRACT

This invention relates to certain quinolinyl-benzoheterobicyclic compounds and their use as valuable pharmaceutical agents, particularly as lipoxygenase inhibitors and/or leukotriene antagonists and/or as mediator release inhibitors useful as anti-inflammatory and anti-allergic agents.

29 Claims, No Drawings

QUINOLINYL-BENZOHETEROBICYCLIC DERIVATIVES AS ANTAGONISTS OF LEUKOTRIENE D4

FIELD OF INVENTION

Leukotrienes (LT) are metabolites of arachidonic acid formed by oxygenation by a novel lipoxygenase specific for the C-5 position of the arachidonic acid. This forms 5-hydroperoxytetraenoic acid (5-HPETE). The latter is further transformed into an unstable epoxide intermediate leukotriene $A_4$. The $LTA_4$ can then form the peptidoleukotrienes. The $LTC_4$ is formed by glutathione addition with 5-transferase. $LTC_4$ may then be metabolized to $LTD_4$ and $LTE_4$ by successive elimination of a δ-glutamyl residue and glycine. This pathway has received much attention during the past few years and means have been sought as to how leukotriene antagonist properties could be established, i.e., researchers have been seeking a means to antagonize one or more of the arachidonic acid metabolites known as the peptido-leukotrienes $LTC_4$, $LTD_4$ and $LTE_4$. These are also known as the cysteinyl leukotrienes and they primarily affect smooth muscle and other cells having contractile capacity. In general these $C_4$, $D_4$ and $E_4$ leukotrienes have been shown to play a key role in hypersensitivity reactions. They have bronchospastic action and activate airway smooth muscle. Inhalation studies on healthy volunteers and asthmatic subjects have corroborated that $LTC_4$ and $LTD_4$ are potent inducers of airway obstruction such as stimulation of mucous secretion. In addition, asthmatics are hyperreactive to inhaled leukotrienes which are involved with the pathogenesis of asthma such as allergic pulmonary disorders of asthma, hay fever and allergic rhinitis. These peptido-leukotrienes also are powerful spasmogens, increase vascular permeability and are involved with the pathogenesis of certain inflammatory diseases such as bronchitis, ectopic and atopic eczema and psoriasis. They are the bioactive components of Slow-Reacting-Substance of Anaphylaxis (SRS-A). In addition, $LTC_4$, $LTD_4$ and $LTE_4$ may also decrease blood pressure by an action on the heart, because cysteinyl leukotrienes reduce myocardial contractility and coronary blood flow. The hypotensive phase is usually preceded by an initial pressor effect which is primarily a consequence of generalized arteriolar constriction.

Emphasis has been directed for several years to the synthesis of compounds which are $LTD_4$ antagonists. It is thought that such compounds would be of significant value in the regulation of coronary flow rate and contractile force of the heart. They would also be useful in the treatment of hypersensitivity and bronchospastic disorders involving smooth muscle such as asthma, hay fever and allergic rhinitis. It is further thought that inflammatory conditions such as bronchitis, ectopic and atopic eczema and psoriasis could be controlled.

There is currently a number of Leukotriene $D_4$ antagonists being developed. These include a number of compounds contained in patent applications which are assigned to the same assignee as the present invention. These include U.S. Pat. Nos. 4,920,132, 4,920,130, 4,920,133, 4,918,081, 4,920,131, 4,924,010 and U.S. Application Ser. No. 379,528, none of which disclose the benzoheterobicyclic compounds of the present invention.

SUMMARY OF THE INVENTION

This invention relates to quinolinylbenzoheterobicyclic compounds having $LTD_4$ antagonist properties and to therapeutic compositions and methods for the treatment of disorders which result from $LTD_4$ activity. In general, the compounds of this invention can be described by general Formula I

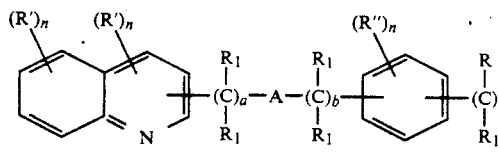 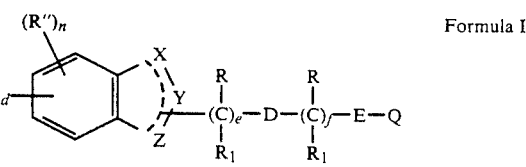

Formula I where:
A is O, S,

or a carbon-carbon single bond;
B is a carbon-carbon single bond, O, S, SO, $SO_2$, $NR_1$,

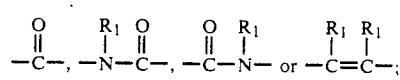

D is O, S, $NR_1$,

or a carbon-carbon single bond;
E is a carbon-carbon single bond or

a is 0–1; b is 0–1; c is 0–3; d is 0–3; e is 0–3; f is 0–3; n is 0–2;
X is $NR_2$, O or S;
Y is $CR_2R_3$ or $NR_2$ when Z is $CR_2R_3$;
Z is $CR_2R_3$, $NR_2$, O or S;
R' is independently hydrogen, alkyl, hydroxy, alkoxy, carboxy, carbalkoxy, halo, nitro, haloalkyl, cyano or acyl;
R" is independently hydrogen, hydroxy, alkoxy, halo, haloalkyl, or —$(CH_2)_x$—F—$(CH_2)_y$—G;
$R_1$ is independently hydrogen, alkyl or aralkyl;
$R_2$ is a bond, hydrogen or alkyl;
$R_3$ is hydrogen together with a vicinal $R_3$ group or a double bond;
R is independently hydrogen or —$(CH_2)_x$—F—$(CH_2)_y$—G provided F and A or B are not geminal oxygen atoms:
x is 0–3; y is 0–3;

F is a carbon-carbon single bond, O, S or NR₁;
G is hydrogen, alkyl, alkenyl, cycloalkyl, aryl, aralkyl, hydroxy, alkoxy, aralkoxy, amino, mono- and di-alkylamino, aralkylamino, acylamino, —CONR₁R₁, —COOR, CN, tetrazolyl,

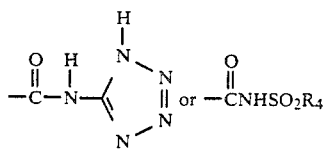

where R₄ is hydrogen, alkyl, haloalkyl, phenyl or benzyl;
vicinal R groups together may be —(CH₂)$_y$— where y is 1-4, thus forming a 3-6 membered ring;
geminal R₁ and R groups may together form a spiro substituent, —(CH₂)$_z$—, where z is 2-5;
geminal R₁ or R₁ and R groups may together form an alkylidenyl substituent

Q is —COOR₁, —CN,

where R₄ is as described above,

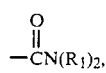

—OR₁, tetrazolyl, substituted tetrazolyl where the substituent may be alkyl, carboxyalkyl or carbalkoxyalkyl or

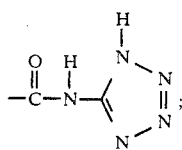

or a pharmaceutically acceptable salt thereof.

DETAILED DESCRIPTION AND PREFERRED EMBODIMENTS

The compounds of Formula I contain at least three aromatic rings. For the purposes of this invention these may be designated as shown in Formula II. The substitution pattern of these rings along the chain with respect to each other is as follows.

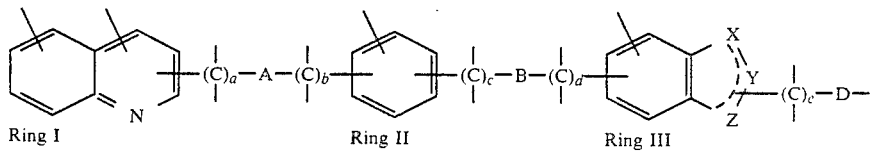

Ring I    Ring II    Ring III                    Formula II

The substitution pattern of the quinoline ring, that is Ring I, is preferably at the 2-position for extending the side chain. As this side chain containing A progresses from the quinoline ring to the phenyl ring, designated as Ring II, this phenyl ring may be substituted by this chain in the ortho, meta or para positions of this phenyl ring. As the chain containing B progresses from the phenyl ring to the benzoheterobicyclic ring, designated as Ring III, this chain may originate at the ortho, meta or para positions of the phenyl ring and terminate at the various 4, 5, 6 or 7 positions of the benzoheterobicyclic ring. Further, the chain containing D may be substituted at the 2 or any other available position of the benzoheterobicyclic ring.

The preferred substitution pattern for Ring II is meta or para, that is:

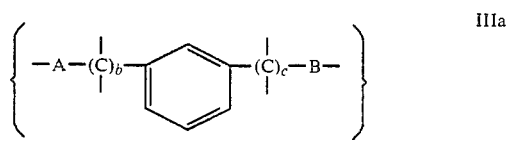

IIIa or

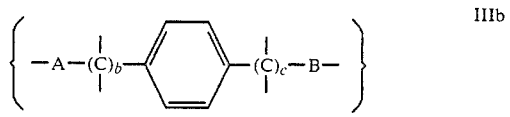

IIIb

Ring III, however, may preferably be substituted in the two position or one or three positions when available, that is:

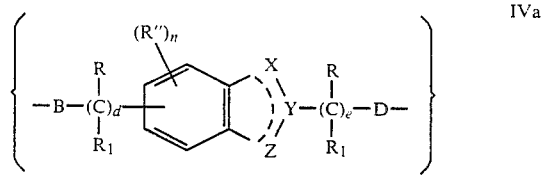

IVa or

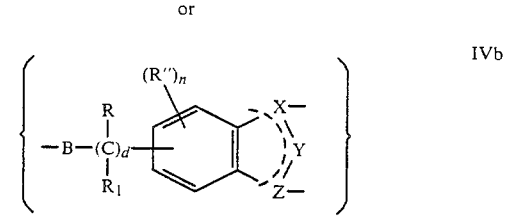

IVb when X is —NR₂ and Z is —NR₂ or CR₂R₃.

Further preferred compounds of this invention are described by Formula I where one of R and/or R" is —(CH₂)$_x$—F—(CH₂)$_y$—G and G is —CONR₁R₁, —COOR₁, —CN, tetrazolyl,

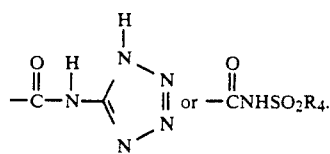

The more preferred compounds are those where A and B are O, S,

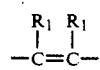

or a carbon-carbon single bond; Q is —COOR$_1$, —CON(R$_1$)$_2$, tetrazolyl or

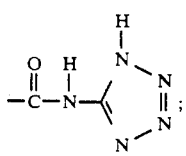

and R and R" are as described above.

In certain preferred compounds the molecule may contain what could be considered to be two side chains which are formed from R and/or R" moieties in combination with the —(C)$_e$—D—(C)$_f$—E—Q portion of the molecule or when e and f are both O and D and E are both carbon-carbon single bonds then the two side chains are formed from any combination of R and R" moieties. It is still preferred that these side chains contain acidic and/or basic functions. This will become more evident as the invention is described in greater detail.

In addition, the present invention relates to the method of using these compounds as lipoxygenase inhibitors and/or leukotriene antagonists possessing anti-inflammatory and anti-allergic properties.

As employed above and throughout the disclosure, the following terms, unless otherwise indicated, shall be understood to have the following meanings:

"Alkyl", either alone or with various substituents defined herein, means a saturated aliphatic hydrocarbon, either branched or straight chained. A "loweralkyl" is preferred having about 1 to about 6 carbon atoms. Examples of alkyl include methyl, ethyl, n-propyl, isopropyl, butyl, sec-butyl, t-butyl, amyl, hexyl, etc.

"Alkoxy" refers to a loweralkyl-O-group.

"Alkenyl" refers to a hydrocarbon having at least one point of unsaturation and may be branched or straight chained. Preferred alkenyl groups have six or less carbon atoms present such as vinyl, allyl, ethynyl, isopropenyl, etc.

"Aralkyl" means an alkyl group substituted by an aryl radical. The preferred aralkyl groups are benzyl or phenethyl.

"Cycloalkyl" means a saturated monocyclic hydrocarbon ring having 3 to about 6 carbon atoms such as cyclopropyl, cyclohexyl, etc.

"Acyl" means an organic group derived from an organic acid by removal of its hydroxyl group. Preferred acyl groups are acetyl, propionyl, benzoyl, etc.

"Aryl" means an aromatic hydrocarbon radical group such as phenyl, nahthyl, substituted phenyl or substituted naphthyl where the substituents may be one of the same or different R' substituents. Phenyl is the preferred aryl and tolyl is the preferred substituted aryl.

"Halo" means a halogen. Preferred halogens include, chloride, bromide and fluoride. The preferred haloalkyl group is trifluoromethyl.

The compounds of this invention may be prepared in segments as is common to a long chain molecule. Thus it is convenient to synthesize these molecules by employing condensation reactions at the A, B and D cites of the molecule. For this reason the present compounds may be prepared by art recognized procedures from known compounds or readily preparable intermediates. Exemplary general procedures are as follows. Thus in order to prepare the compound:

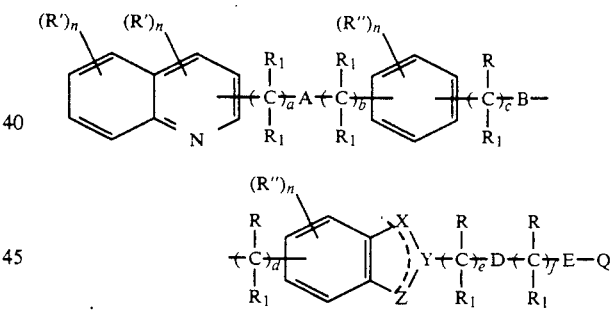

the following reactions may be employed:

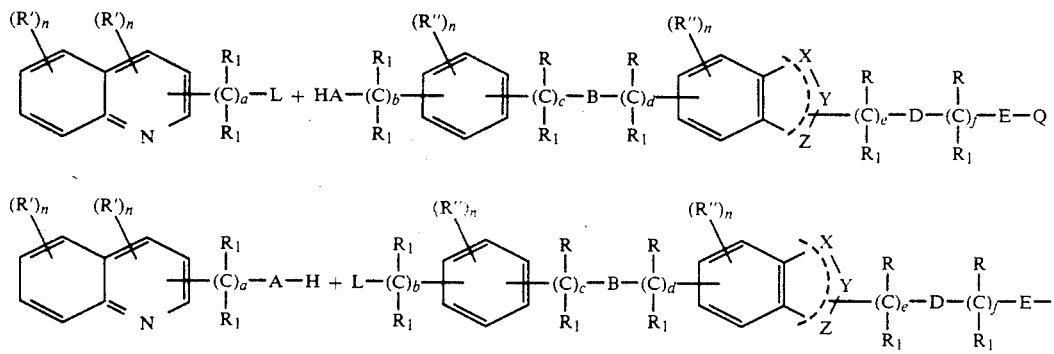

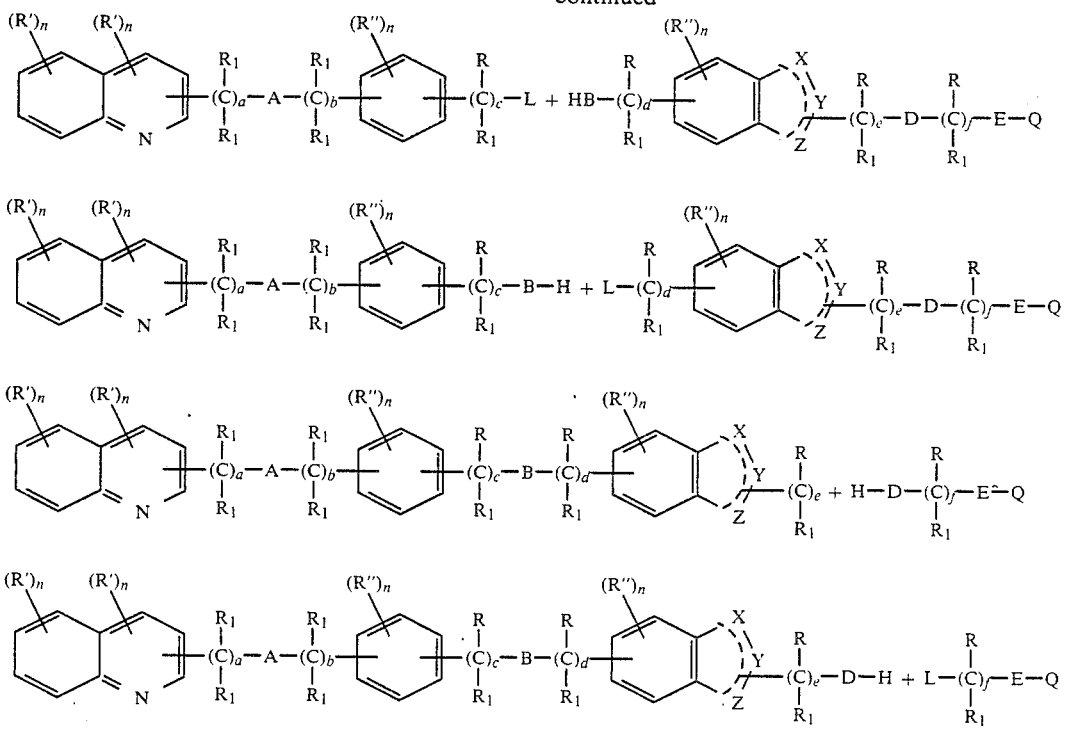

where: R, R', R", $R_1$, $R_2$, a, b, c, d, e, f, n, A, D, X, Y and Z are as defined above; B is O or S; E is a carbon-carbon single bond; Q is —CN,

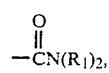

—$COOR_1$ or tetrazolyl; and L is a leaving group, such as halo, tosylate, or mesylate.

Where B is O or S, any base normally employed to deprotonate an alcohol or thiol may be used, such as sodium hydride, sodium hydroxide, triethyl amine, sodium bicarbonate or diisopropyl/ethylamine.

Reaction temperatures are in the range of room temperature to reflux and reaction times may vary from 2 to 96 hours. The reaction is usually carried out in a solvent that will dissolve both reactants and is inert to both as well. Solvents include, but are not limited to, diethyl ether, tetrahydrofuran, N,N-dimethyl formamide, dimethyl sulfoxide, dioxane and the like.

In the case where B is SO or $SO_2$ then treatment of the thio compound with m-chlorobenzoic acid or sodium periodate results in the sulfinyl compound. Preparation of the sulfonyl compound may be accomplished by known procedures such as dissolving the sulfinyl compound in acetic acid and treating with 30% $H_2O_2$.

Those compounds where B is

may be prepared by the following reaction sequence:

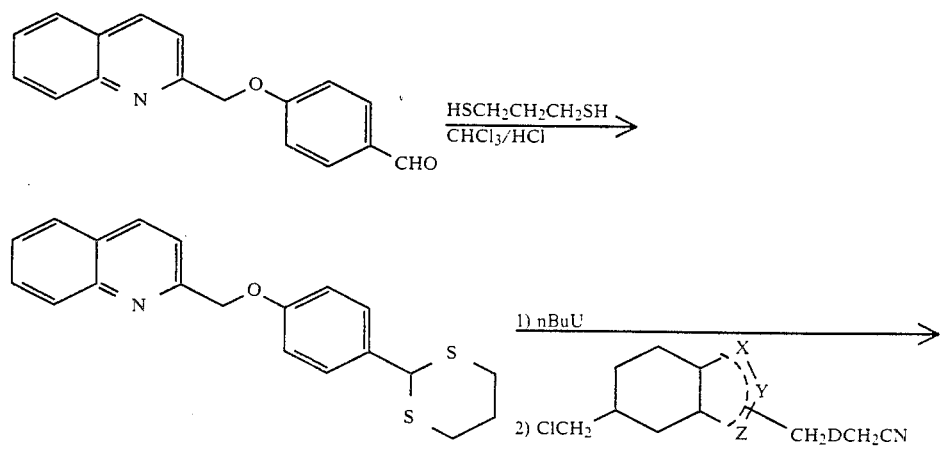

-continued

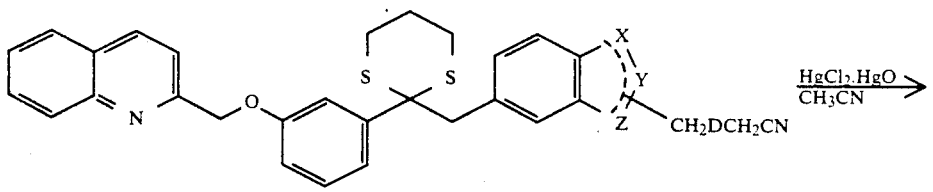

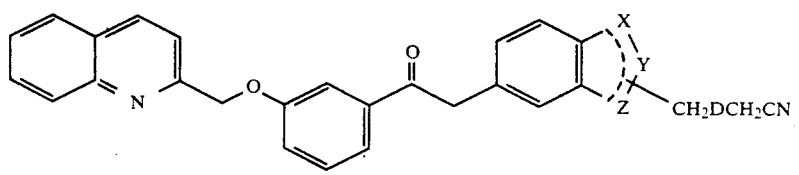

Condensation of the aldehyde with 1,3-propanedithiol results in the dithiane compound. This may be carried out in chloroform at reduced temperatures (−20° C.) while bubbling HCl gas into the reaction mixture. The dithiane compound is then treated with N-butyllithium in nonpolar solvent at −78° C. and then reacted with the substituted bicyclicbenzoheterocyclic-methyl chloride. This results in addition of the Ring III to the molecule. The dithiane moiety is then treated with a mercuric chloride - mercuric oxide mixture to form the complex which is then split off leaving the desired compound.

Corresponding compounds may be prepared using the appropriately substituted chloride:

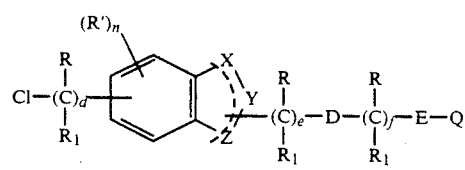

Wittig condensation also may take place at the B position of the molecule of Formula I as follows:

Of course this Wittig condensation may also take place when the Wittig reagent is formed on Ring II position of the molecule which is then condensed with the alkehyde from the bicyclic Ring III portion.

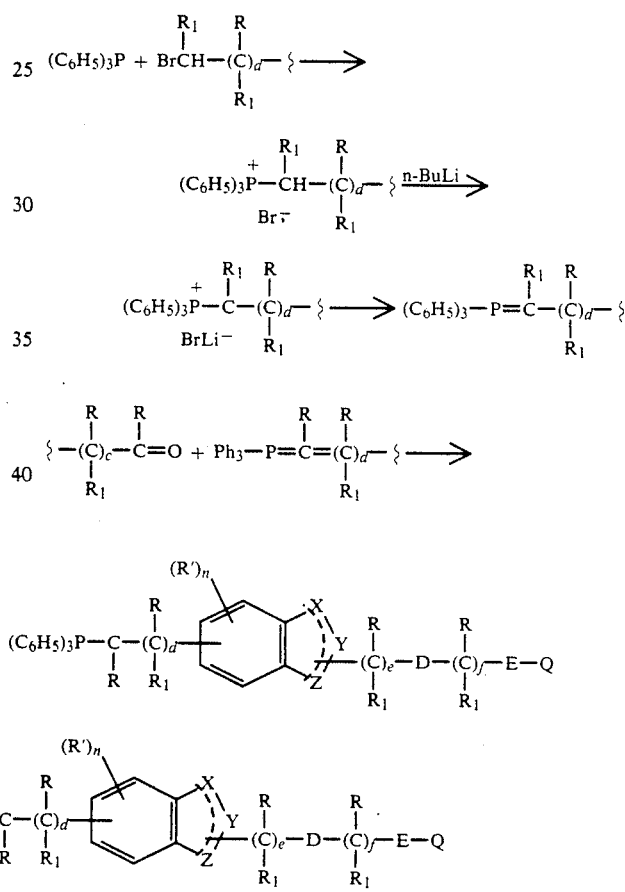

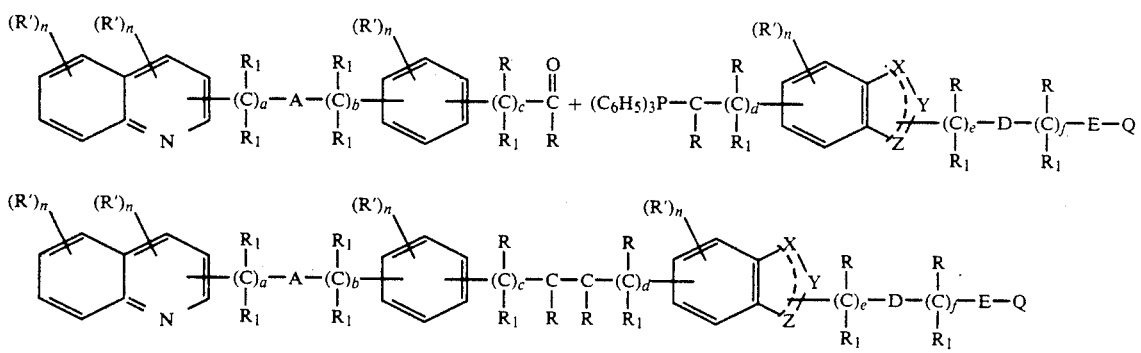

This may be carried out using normal Wittig reaction conditions. When the appropriate aldehyde or ketone is reacted with a Wittig reagent then condensation results in formation of the double bond. This may then be reduced catalytically by known procedures such as Pd/C or any other suitable hydrogenating condition.

The Wittig reagent is prepared by known art recognized procedures such as reaction of triphenyl phosphine or diethylphosphone, with a substituted alkyl bromide followed by treatment with a strong organometallic or alkoxide base such as n-BuLi or NaOH results in the desired ylide.

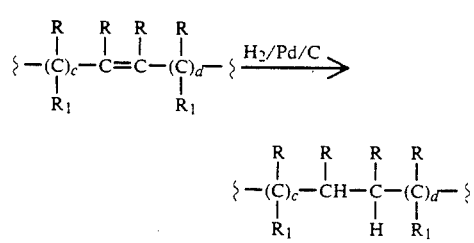

-continued

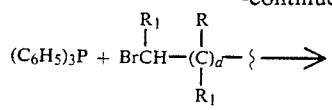

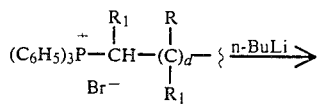

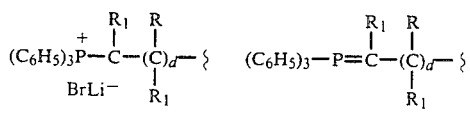

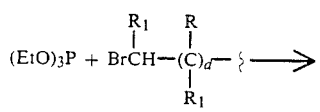

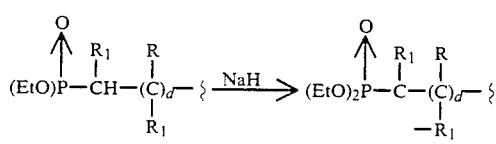

When B is

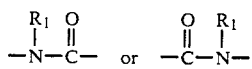

then condensation of the acid halide with the appropriate bicyclicamine will give the desired compound:

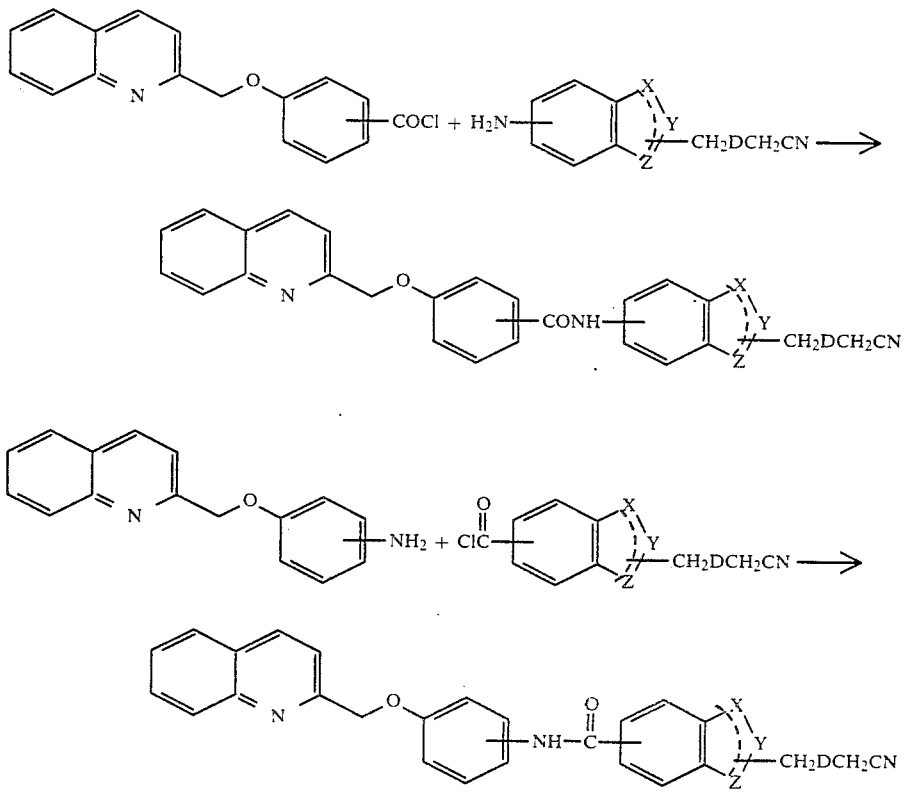

Of course, using the appropriate bicyclicamine will result in the corresponding product.

Those compounds where D and/or E are

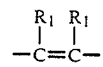

are prepared by reacting the appropriate aldehyde or ketone with a substituted Wittig reagent of the formula:

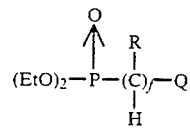

where Q is cyano or carbalkoxy.

The tetrazole may be formed from the nitrile at various stages of the synthesis by treatment with hydrazoic acid formed in situ from sodium azide and an acid.

The products of this invention may be obtained as racemic mixtures of their dextro and levorotatory isomers since at least one asymmetric carbon atom may be present. When two asymmetric carbon atoms are present the product may exist as a mixture of two diastereomers based on syn and anti configurations. These diastereomers may be separated by fractional crystallization. Each diastereomer may then be resolved into dextro and levorotatory optical isomers by conventional methods. Chromatographic methods may also be used.

Resolution may best be carried out in the intermediate stage where it is convenient to combine the racemic compound with an optically active compound by salt formation, ester formation, or amide formation to form two diastereomeric products. If an acid is added to an optically active base, then two diastereomeric salts are produced which posses different properties and different solubilities and can be separated by fractional crystallization. When the salts have been completely separated by repeated crystallization, the base is split off by acid hydrolysis and the pure d and l acids are obtained.

The present compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, sulfuric, nitric, benzenesulfonic, toluenesulfonic, acetic, maleic, tartaric and the like which are pharmaceutically acceptable. Basic salts for pharmaceutical use are the Na, K, Ca and Mg salts.

Various substituents on the present new compounds, e.g., as defined in R, $R_1$ and $R_2$ can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups known in the art, may be employed. Examples of many of these possible groups may be found in "Protective Groups in Organic Synthesis" by T. W. Green, John Wiley and Sons, 1981. For example, nitro groups can be added to the aromatic ring by nitration and the nitro group converted to other groups, such as amino by reduction, and halo by diazotization of the amino group and replacement of the diazo group. Acyl groups can be substituted onto the aryl groups by Friedel-Crafts acylation. The acyl groups can then be transformed to the corresponding alkyl groups by various methods, including the Wolff-Kishner reduction and Clemmenson reduction. Amino groups can be alkylated to form mono and dialkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throuqhout the molecule of the starting material, intermediates, or the final product.

Compounds within the scope of the present invention have potent activity as leukotriene antagonists and as such possess therapeutic value in the treatment of inflammatory conditions and allergic responses such as anaphylaxis and asthma.

Protocol for SRS-A (slow reacting substance of anaphylaxis) Antagonists

Leukotrienes, the products of the 5-lipoxygenase pathway of arachidonic acid metabolism, are potent contractile agents with a variety of smooth muscle preparations. Thus, it has been hypothesized that the leukotrienes contribute significantly to the pathophysiology of asthma. This protocol describes an in vitro assay used to test compounds which specifically antagonize the actions of leukotrienes.

Peripheral strips of guinea pig lungs are prepared and hung in tissue baths (Metro #ME-5505, 10 ml) according to the published procedure—(Proc. Nat'l. Acad. Sci., U.S.A. Volume 77, pp. 4354–4358, 1980). The strips are thoroughly rinsed in Assay Buffer and then connected with surgical silk thread support rods from the tissue baths. The rods are adjusted in the baths and the strips connected to the pressure transducers (Grass FT 103 or Gould US-3). The tissue baths are aerated with 95% oxygen - 5% carbon dioxide and maintained at 37° C. The assay buffer has been made as follows: for each liter of buffer the following are added to approximately 800 ml of water distilled in glass-6.87 g NaCl, 0.4 g $MgSO_4 \cdot 7H_2O$, and 2.0 g D-glucose. Then a solution of 0.368 g $CaCl_2 \cdot H_2O$ in 100 ml glass-distilled water is slowly added to the buffer. Sufficient water is added to adjust the volume to 1 liter, and the solution is aerated with 95% oxygen - 5% carbon dioxide. Usually 10 liters of buffer are used for an experiment with 4 tissues. After the tissues have been repeatedly washed and allowed to equilibrate in the tissue bath, they are challenged with 1M histamine. After maximum contractions have been obtained, the tissues are washed, and allowed to relax back to baseline tension. This histamine challenge procedure is repeated at least 1 to 2 more times to obtain a repeatable control response. The average response to 1M histamine for each tissue is used to normalize all other challenges.

Responses of each tissue to a predetermined concentration of leukotriene are then obtained. Usually test compounds are examined initially at 30M on resting tension of the tissues without any added agonist or antagonist to determine if the compound has any possible intrinsic activity. The tissues are washed and the test compound is added again. Leukotriene is added after the desired preincubation time. The intrinsic activity of the compounds, and their effect on leukotriene-induced contractions are then recorded.

The results of this test for compounds of this invention indicates that these compounds are considered to be useful leukotriene antagonists.

Inhibitions of ($^3$H)-LTD$_4$ Binding Membranes from Guinea Pig Lung.

A. Preparation of the Crude Receptor Fraction

This procedure was adapted from Mong et al. 1984. Male guinea pigs are sacrificed by decapitation and their lungs are quickly removed and placed in a beaker containing ice-cold homogenization buffer. The lungs are separated from connective tissue, minced with scissors, blotted dry and weighed. The tissue is then homogenized in 40 volumes (w/v) of homogenization buffer with a Polytron at a setting of 6 for 30 seconds. The homogenate is centrifuged at 1000 xg for 10 minutes (e.g. 3500 RPM, SS-34 Rotor). The supernate is filtered through two layers of cheese cloth and centrifuged at 30,000 xg for 30 minutes (e.g. 18,500 RPM SS-34 Rotor), after which the resulting pellet is resuspended in 20 volumes of assay buffer by hand homogenization using a Dounce homogenizer. The final pellet is resuspended in 10 volumes of assay buffer and kept at 4° C. until use.

B. Binding Assay

Each assay tube (16×100 mm) contains the following:

490 μL Assay Buffer
10 μL Test compound or solvent
100 μL $^3$H-LTD$_4$ (ca. 17,500 DMP)
400 μL Protein preparation Incubations are done at 25° C. for 20 minutes in a shaking water bath. Reactions are started by the addition of the protein preparation. At the end of the incubation time, 4.0 ml of cold wash buffer is added to the tube. After being vortexed, the contents of the tube are immediately poured over a Whatman GF/C Filter (25 mm diameter) which is sitting in a vacuum manifold (e.g., Millipore Model No. 3025 manifold) to which a partial vacuum is applied. The filters are immediately washed with an additional 15 ml of cold buffer. The filters are transferred to 7 ml plastic scintillation vials to which 6.0 ml of appropriate scintillation fluid (e.g., Scintiverse) is added. After being allowed to equilibrate for 4-6 hours, the radioactivity is counted with a liquid scintillation counter appropriately set for tritium.

The required control assay tubes include the following:

(a) Total Binding: No test compound is added; buffer is substituted.
(b) Non-Specific Binding: Non-labeled ligand is added at a concentration of 1M.
(c) Solvent Controls: If test compound is dissolved in a solvent, controls for both Total Binding and Non-Specific Binding containing solvent but no compounds are required.

The results of this test indicate that compounds of this invention exhibit valuable properties which are useful in the treatment of inflammatory conditions and allergic responses.

Preferred compounds of the present invention also show activity as inhibitors of mediator release from passively sensitized rat mast cells (RMC), making them useful in the treatment of allergy and asthma. Thus, preferred compounds possess dual activity as mediator release inhibitors and $LTD_4$ antagonists. Standard testing procedures to measure histamine release when mast cells are challenged with antigen may be found in the following reference: Kusner, et.al., J. Pharmacol. and Exp. Ther. 184, 41(1973).

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepthelially including transdermal, opthalmic, sublingual and buccal; topically including ophthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, trochees, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, trochees, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxy-propylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from 0.1 to 100 M/day or from about 0.1 mg to about 50 mg/kg of body weight per day and higher although it may be administered in several different dosage units. Higher dosages are required for oral administration.

The compounds of the present invention may be prepared by the following representative examples:

EXAMPLE 1

3-(2-quinolinylmethyloxy)phenol

A mixture (0.06 moles) of 2-chloromethylquinoline hydrochloride, (0.06 moles) of 1,3-benzenediol and 18 g of potassium carbonate in 50 ml of dimethylformamide is heated at 70° C. overnight. The reaction mixture is poured into water, and the precipitated product is collected, filtered and dried to give 3-(2-quinolinylmethyloxy)phenol having an m.p. of 151–53° C.

EXAMPLE 2

When 2-chloromethylquinoline hydrochloride of Example 1 above is replaced by the quinoline compounds of Table I below, then the corresponding product is obtained.

TABLE I 2-bromomethylquinoline
2-(1-chloroethyl)quinoline
2-(2-chloroethyl)quinoline
2-(2-bromoethyl)quinoline
3-chloromethylquinoline
4-chloromethylquinoline
2-(β-chloro-β-phenethyl)quinoline
2-chloromethyl-4-methylquinoline
2-chloromethyl-6-methylquinoline
2-chloromethyl-8-methylquinoline
2-chloromethyl-6-methoxyquinoline
2-chloromethyl-6-nitroquinoline
2-chloromethyl-6,8-dimethylquinoline
2-chloromethyl-7-chloroquinoline
2-chloromethyl-7-bromoquinoline
2-chloromethyl-7-nitroquinoline
2-chloromethyl-7-methylquinoline

EXAMPLE 3

When 1,3-benzenediol of Example 1 above is replaced by the compounds of Table II below, then the corresponding product is obtained.

TABLE II 1,2-benzenediol
1,4-benzenediol
2-mercaptophenol
3-mercaptophenol
4-mercaptophenol
1,3-dimercaptobenzene TABLE II-continued 1,4-dimercaptobenzene
2-methylresorcinol
5-methylresorcinol
5-methoxyresorcinol
5-methyl-1,4-dihydroxybenzene
methyl salicylate
methyl-3-hydroxybenzoate
methyl-4-hydroxybenzoate
3-hydroxybenzaldehyde
2-hydroxybenzaldehyde
4-hydroxybenzaldehyde

EXAMPLE 4

When 1,3-benzenediol of Example 1 is replaced by the compounds of Table III, then the corresponding products are obtained.

TABLE III 3-hydroxybenzylalcohol
3-hydroxyethylphenol
4-hydroxybenzylalcohol
4-hydroxyethylphenol
2-hydroxy-α-ethylbenzylalcohol
2-hydroxy-α-propylbenzylalcohol
3-hydroxy-α-methylbenzylalcohol
3-hydroxy-α-ethylbenzylalcohol
3-hydroxy-α-propylbenzylalcohol
4-hydroxy-α-methylbenzylalcohol
4-hydroxy-α-ethylbenzylalcohol
4-hydroxy-α-propylbenzylalcohol

EXAMPLE 5

When the compounds of Table I, Example 2 are reacted with the compounds of Table II, Example 3 under the conditions of Example 1, then the corresponding products are obtained.

EXAMPLE 6

When the compounds of Table I, Example 2 are reacted with the compounds of Table III, Example 4, the corresponding products are obtained.

EXAMPLE 7

3-(2-quinolinylmethyloxy)benzyl alcohol 20.0g (93.5 mmoles) of 2-chloromethylquinoline hydrochloride, 11.6 g (93.5 mmoles) of 3-hydroxybenzyl alcohol and 7.48 g (186.42 mmoles) of powdered sodium hydroxide are combined in 56 ml of dimethylsulfoxide. After stirring room temperature for 24 hours the mixture is poured into ice-water and the resulting solid is collected and dried to give 25.6 g of 3-(2-quinolinylmethyloxy)benzyl alcohol.

EXAMPLE 8

When the compounds of Table I, Example 2 are reacted with the compounds of Table II, Example 3 under the conditions of Example 7, the corresponding products are obtained.

EXAMPLE 9

When the compounds of Table I, Example 2 are reacted with the compounds of Table III, Example 4 under the conditions of Example 7, the corresponding products are obtained.

EXAMPLE 10

5-(6-(3-(2-quinolinylmethyloxy)phenoxymethyl)benzoxazol-2-yl)tetrazole

Step 1: 2-cyano-6-methylbenzoxazole

This compound may be synthesized according to the literature procedure. (K. Dickore, K. Sasse and K.-D. Bode, Liebigs Ann. Chem. 733, 70–87 (1970).)

Step 2: 2-cyano-6-bromomethylbenzoxazole

To a stirred solution of 2-cyano-6-methylbenzoxazole (2.0 g, 12.66 mmol) in carbon tetrachloride (50 ml) at room temperature are added successively N-bromosuccinimide (2.37 g, 13.3 mmol) and benzoyl peroxide (30.7 mg, 0.13 mmol). The solution is irradiated with a sunlamp for 2 hours and concentrated. The residue is dissolved in 500 ml of ether and the solution filtered. The filtrate is concentrated and subjected to HPLC (2% ethyl acetate in hexane) to afford 2-cyano-6-bromomethylbenzoxazole which is used directly in the next step.

Step 3: 2-cyano-6-[3-(2-quinolinylmethyloxy)phenoxymethyl]-benzoxazole

To a stirred solution of sodium 3-(2-quinolinylmethyloxy)phenoxide pentahydrate (3.63 g, 10 mmol) in acetone (85 ml) and dimethylformamide (10 ml) at room temperature are added successively potassium carbonate (2.07 g, 15 mmol) and 2-cyano-6-bromomethylbenzoxazole (1.90 g, 8.02 mmol). The resulting solution-suspension is refluxed for 16 hours and concentrated. Water (100 ml) and ethyl acetate (200 ml are added. Extraction with ethyl acetate is followed by washing with water and brine, drying (MgSO$_4$) and evaporation under reduced pressure. The residue is subjected to flash chromatography over silica gel. Elution with 33% ethyl acetate in hexane and concentration of the appropriate fractions provides 2-cyano-6-[3-(2-quinolinylmethyloxy)phenoxymethyl]benzoxazole which is used directly in the next step.

Step 4: 5-(6-(3-(2-quinolinylmethyloxy)phenoxymethyl)benzoxazol-2-yl)tetrazole

A solution-suspension of 2-cyano-6-[3-(2-quinolinylmethyloxy)phenoxymethyl]benzoxazole (660 mg, 1.62 mmol), sodium azide (316.3 mg, 4.86 mmol) and ammonium chloride (260.2 mg, 4.86 mmol) in DMF (11 ml) is heated to 110° C. for 5 hours and stirred at room temperature for 12 hours. The mixture is poured over ice-water and the pH adjusted to 10 with 1N NaOH. The aqueous mixture is washed with ether and the pH adjusted to 4 with 1N HCl. The precipitated solid is filtered and washed successively with water, ethanol and methylene chloride. Recrystallization from ethanol-DMF affords 5-(6-(3-(2-quinolinylmethyloxy)phenoxymethyl)benzoxazol-2-yl)tetrazole (M.P. 223–225° C. dec.).

EXAMPLE 11

When 3-(2-quinolinylmethyloxy)phenoxide in Example 10, Step 3 is replaced with 4-(2-quinolinylmethyloxy)phenoxide then the product prepared is 5-(6-(4-(2-quinolinylmethyloxy)phenoxymethyl)benzoxazol-2-yl)tetrazole (M.P. 213–215.° C. dec.).

EXAMPLE 12

When the compounds prepared by Examples 1-9 are reacted with 2-cyano-6-(bromomethyl)benzoxazole following the procedures of Example 10, Step 3 then the corresponding nitrile product is prepared.

EXAMPLE 13

When the compounds of Example 11 are reacted according to the procedure of Example 10, Step 4, then the corresponding tetrazole is prepared.

EXAMPLE 14

2-ethoxyethyl 6-[3-(2-quinolinylmethyloxy)phenoxymethyl]benzoxazole-2-carboxylate Dry HCl gas is bubbled through a cold (0° C.) solution of 2-cyano-6-[3-(2-quinolinylmethyloxy)phenoxymethyl]benzoxazole (860 mg, 2.1 mmol) in ethoxyethanol (20 ml) and water (1 ml) for 25 minutes. The yellow solution is stirred at room temperature for 30 minutes and stored in a refrigerator for 16 hours. The mixture is poured into ice-water. The white precipitate is collected by filtration, washed with water and dried. Flash chromatography over silica gel using 40% ethyl acetate in hexane affords 2-ethoxyethyl 6-[3-(2-quinolinylmethyloxy)phenoxymethyl]benzoxazole-2-carboxylate (M.P. 84–85° C.).

EXAMPLE 15

When the compounds prepared by Example 12 are substituted for 2-cyano-6-[3-(2-quinolinylmethyloxy)-phenoxymethyl]benzoxazole in Example 14, then the corresponding esters are prepared.

EXAMPLE 16 trans-(E)-2-cyano-6-(2-(3-(quinolin-2ylmethyloxy)-phenyl)ethenyl)benzoxazole

To a suspension of 3.93 g (8.30 mmoles) of 2-cyanobenzoxazol-6-ylmethyltriphenylphosphonium bromide (prepared from 2.7 g 7-bromomethyl-2-cyano-4-oxo-4H-1-benzoxazole and 2.98 g triphenylphosphine refluxed in toluene for 1 hour) in 100 ml of dimethyl formamide is added 0.27 g (9.13 mmoles) of an 80% sodium hydride in oil dispersion. After stirring at 0° C. for 1 hour, 2.18 g (8.30 mmoles) of 3-(quinolin-2-ylmethyloxy)benzaldehyde in 20 ml of dimethylformamide is added and stirred for 2 hours. The mixture is poured into ice water, extracted with ethyl acetate which is dried and concentrated in vacuo. Purification by flash column chromatography through silica gel gives 1.1 g trans-(E)-2-cyano-7-(2-(3-(quinolin-2-ylmethyloxy)-phenyl)ethenyl)-benzoxazole which is used directly in the next step.

EXAMPLE 17 trans-(E)-5-(6-(2-(3-(quinolin-2-yl-methoxy)phenyl)ethenyl)benzoxazol-2-yl)tetrazole A suspension of 0.81g (2.1 mmoles) of trans-(E)-2-cyano-7-(2-(3-(quinolin-2-ylmethyloxy)phenyl) ethenyl)benzoxazole, 0.56 g (10.45 mmoles) of ammonium chloride and 0.68 g (10.45 mmoles) of sodium azide in 20 ml of dimethylformamide is heated at 100° C. for 18 hours. The mixture is poured into ice water. Addition of ethyl acetate gives a precipitate which is collected and crystallized from methylene chloride/petroleum ether to give trans-(E)-5-(6-(2-(3-(quinolin-2-ylmethyloxy)phenyl)ethenyl)benzoxazol-2-yl)tetrazole.

EXAMPLE 18

5-(6-(2-(3-(quinolin-2-ylmethyloxy)phenyl)ethyl)benzoxazol-2-yl)tetrazole

To a solution of 0.18g (0.42 mmoles) of trans-(E)-5(6-(2-(3-(quinolin-2-ylmethyloxy)phenyl) ethenyl)-benzoxazol-2-yl)tetrazole in 30 ml of ethanol is added 0.08 g of 10% palladium on carbon and the mixture is shaken under 30 psi of hydrogen for 4 hours. The mixture is filtered and the filtrate concentrated in vacuo. The residue is crystallized from methylene chloride to give 5(6-(2-(3-(quinolin-2-ylmethyloxy)-phenyl)ethyl) benzoxazol-2-yl)tetrazole.

EXAMPLE 19

When the compounds of Table I, Example 2 are reacted with the benzaldehyde derivatives of Table II, Example 3 under the conditions of Example 1 or Example 7 the corresponding products are obtained.

EXAMPLE 20

When the products of Example 19 are substituted for 3-(quinoline-2-ylmethyloxy)benzaldehyde in Example 16, the corresponding products are obtained.

EXAMPLE 21

When the products of Example 20 are substituted for trans-(E)-2-cyano-6-(2-(3-(quinoline-2-ylmethyloxy)-phenyl)ethenyl)benzoxazole in Example 17, the corresponding products are obtained.

EXAMPLE 22

When the products of Example 21 are substituted for trans-(E)-5-(6-(2-(3-(quinoline-2-ylmethyloxy)phenyl)ethenyl)benzoxazol-2-yl)tetrazole in Example 18, the corresponding products are obtained.

EXAMPLE 23

3-(2-quinolinylmethyloxy)benzylchloride 25.6g (93.5 mmoles) of 2-(3-hydroxymethylphenoxy)methylquinoline is dissolved in 30 ml of methylene chloride and 3 drops of dimethylformamide is added. 60.7 ml of a 2.0M solution of thionyl chloride in methylene chloride is then added dropwise at 0° C. The mixture is allowed to warm to room temperature and stirred for 5 hours. The solution is washed with sodium bicarbonate solution, dried, concentrated in vacuo and the crude product purified by silica gel HPLC to yield 12.1 g 3-(2-quinolinylmethyloxy)benzylchloride as a pale yellow solid.

EXAMPLE 24

When 2-(3-hydroxymethylphenoxy)methylquinoline of Example 23 above is replaced by the products of Example 6 or Example 9 above, then the corresponding products are obtained.

EXAMPLE 25

2-cyano-6-(3-(quinolin-2-ylmethyloxy)benzyloxy)benzoxazole

To 2-cyano-6-hydroxybenzoxazole (11.87 mmoles) and 2-((3-chloromethylphenoxy)methyl)quinoline (11.87 mmoles) in dimethylsulfoxide (20 ml) is added powdered sodium hydroxide (0.475 q). After one week the reaction mixture is poured into ice water and the resulting precipitate collected and purified by HPLC to give 2-cyano-6-(3-(quinolin-2-ylmethyloxy)benzyloxy)benzoxazole which is used directly in the next step.

EXAMPLE 26

5-(6-(3-(quinolin-2-ylmethyloxy)benzyloxy)benzoxazol-2-yl)tetrazole 2-cyano-6-(3-(quinolin-2-ylmethyloxy)benzyloxy)benzoxazole (2.97 mmoles), sodium azide (965 mg), pyridine hydrochloride (1.72 g) and dimethylformamide (7 ml) are combined and heated at 100° C. for 48 hours. The reaction mixture is poured into cold water and the resulting precipitate is collected. The precipitate is dissolved in hot ethanol and reprecipitated by addition of water to give 5-(6-(3-(quinolin-2-ylmethyloxy)benzyloxy)benzoxazol-2-yl)tetrazole.

EXAMPLE 27

When 3-(2-quinolinylmethyloxy)benzylchloride in Example 25 above, is replaced by the products of Example 24, then the corresponding products are obtained.

EXAMPLE 28

When 2-cyano-6-(3-(quinolin-2-ylmethyloxy)benzyloxy)benzoxazole in Example 26 above, is replaced by the products of Example 27, then the corresponding products are obtained.

EXAMPLE 29 n-propyl-5-hydroxybenzoxazole-2-carboxylate 12.72 g (49.2 mmoles) of 2-carboxy-5-hydroxybenzoxazole is dissolved in 200 ml of n-propanol and 1 drop of concentrated sulfuric acid is added. The mixture is refluxed for 30 hours, concentrated. The resulting solid is suspended in water, neutralized with sodium bicarbonate and filtered, washing the solid with water, then drying. This gives n-propyl-5-hydroxybenzoxazole-2carboxylate which is purified by recrystallization from n-propanol/acetone or by HPLC.

EXAMPLE 30 n-propyl-5-(3-(quinolin-2-ylmethyloxy)benzyloxy)benzoxazole-2-carboxylate

A mixture of 3.47 g of 2-((3-chloromethylphenoxy)methyl)quinoline, 2.7 g of n-propyl-5-hydroxybenzoxazole-2carboxylate, 1.69 g of potassium carbonate and 1 ml of dimethylformamide is refluxed in 50 ml of acetone for 41 hours. The mixture is concentrated in vacuo and the residue is dissolved in water. This solution is neutralized with diluted hydrochloric acid and the resulting solid is filtered off and purified by flash silica gel chromatography in propanol-dimethylformamide to give n-propyl-5-(3-(quinolin-2-ylmethyloxy)benzyloxy)-benzoxazole-2-carboxylate.

EXAMPLE 31

5-(3-(quinolin-2 ylmethyloxy)benzyloxy)benzoxazole-2-carboxylic acid

A mixture of 0.64 g of n-propyl-5-(3-(quinolin-2-ylmethyloxy)benzyloxy)benzoxazole-2-carboxylate and 0.45 g of sodium bicarbonate in 20 ml of ethanol in 20 ml of water is refluxed for 1.5 hours, then stirred at room temperature overnight. The mixture is neutralized and the resulting solid is filtered off, washed with water and dried in vacuo to give 5-(3-quinolin-2-ylmethyloxy)-benzyloxy)benzoxazole-2-carboxylic acid.

EXAMPLE 32 ethyl
6-(3-(quinolin-2-ylmethyloxy)benzyloxy)benzoxazole-2-carboxylate

A mixture of 1.35 g (6.41 mmoles) of 2-carboethoxy-6hydroxybenzoxazole, 1.82 g (6.41 mmoles) of 2-(3-chloromethylphenoxy)methylquinoline and 0.886 g of potassium carbonate in 12 ml of dimethylformamide and 96 ml of acetone is refluxed for 2 days, cooled, concentrated in vacuo and the residue taken up in water and is extracted into ethyl acetate. The solution is concentrated and the crude product is recrystallized from ethyl acetate to give ethyl 6-(3-quinolin-2-ylmethyloxy)benzyloxy)benzoxazole-2carboxylate.

EXAMPLE 33

When n-propyl 5-(3-(quinolin-2-ylmethyloxy)benzyloxy)benzoxazole-2-carboxylate in Example 31 is replaced by ethyl 6-(3-(quinolin-2-ylmethyloxy)benzyloxy)benzoxazole-2-carboxylate, 6-(3-quinolin-2-ylmethyloxy)benzyloxy)benzoxazole-2-carboxylic acid is obtained.

EXAMPLE 34

When ethyl 6-hydroxybenzoxazole-2-carboxylate is replaced by ethyl 7-chloro-6-hydroxybenzoxazole-2carboxylate; ethyl 6-hydroxy-7-n-propylbenzoxazole-2carboxylate; ethyl 4-methyl-6-hydroxybenzoxazole-2carboxylate; ethyl 5-methyl-4-hydroxy-benzoxazole-2carboxylate; ethyl 5-hydroxy-6-methyl-benzoxazole-2carboxylate; ethyl 7-hydroxybenzoxazole-2-carboxylate; or ethyl 5-nitro-6-hydroxybenzoxazole-2-carboxylate in Example 32 then the corresponding product is obtained.

EXAMPLE 35 n-propyl-5-chloro-4-(4-(quinolin-2-ylmethyloxy)benzyloxy)benzoxazole-2-carboxylate Step 1: 5-chloro-4-hydroxybenzoxazole-2-carboxylic acid Ethyl 5-chloro-4-hydroxybenzoxazole-2-carboxylic acid is dissolved in glacial acetic acid and water (5:1) and the solution refluxed for 4 hours. This is cooled and the resulting solid collected and washed with water to give 5-chloro-4-hydroxybenzoxazole-2-carboxylic acid.

Step 2: n-propyl
5-chloro-4-hydroxybenzoxazole-2carboxylate

When the carboxylic acid of Example 29 is replaced by 5-chloro-4-hydroxybenzoxazole-2-carboxylate, n-propyl 5-chloro-4-hydroxybenzoxazole-2-carboxylate is obtained.

Step 3: n-propyl
5-chloro-4-(4-(quinolin-2-ylmethyloxy)benzyloxy)benzoxazole-2-carboxylate 0.78 g of 2-(4-chloromethylphenoxy)methylquinoline, 6.84 g of n-propyl 5-chloro-4-hydroxybenzoxazole-2carboxylate and a catalytic amount of potassium iodide are combined in 50 ml of acetone and 2 ml of dimethylformamide, and refluxed for 19 hours. The crude solid obtained on cooling is purified by flash chromatography to give n-propyl 5-chloro-4-(4-(quinolin-2-ylmethyloxy)benzyloxy)benzoxazole-2-carboxylate.

EXAMPLE 36 ethyl
7-(4-(quinolin-2-ylmethyloxy)phenoxymethyl)benzoxazole-2-carboxylate

Step 1: ethyl 7-bromomethylbenzoxazole-2-carboxylate

When the benzoxazole in Example 10, Step 2 is replaced with ethyl 7-methylbenzoxazole-2-carboxylate, ethyl 7-bromomethylbenzoxazole-2-carboxylate is obtained, which is used directly in the next step.

Step 2: ethyl
7-(4-(quinolin-2-ylmethyloxy)phenoxymethyl)benzoxazole-2-carboxylate 1.8 g of 4-(2-quinolinylmethyloxy)phenol, 1.98 g of ethyl 7-bromomethylbenzoxazole-2-carboxylate and 1.0 g of potassium carbonate are combined in 100 ml of acetone and refluxed for 18 hours. The mixture is cooled, diluted with ethylacetate and filtered. The filtrate is concentrated and the crude product purified by flash chromatography on silica gel in 5% ethanol in chloroform/hexane (1:1) to give ethyl 7-(4-(quinolin-2-ylmethoxy)phenoxymethyl)benzoxazole-2-carboxylate.

EXAMPLE 37

7-(4-(quinolin-2-ylmethyloxy)phenoxymethyl)benzoxazole-2-carboxylic acid 0.66 g of ethyl 7-(4-(quinoline-2-ylmethyloxy)-phenoxymethyl)benzoxazole-2-carboxylate and 0.7 g sodium bicarbonate are combined in 50 ml of ethanol and 5 ml of water. After refluxing for 1.5 hours the mixture is concentrated and the residue diluted with ether. The resulting solid is collected, suspended in water and the pH adjusted to 6 with 1 molar hydrochloric acid. The resulting solid is crystallized from aqueous acetic acid, then tetrahydrofuran/hexane to give 7-(4-(quinolin-2-ylmethyloxy)phenoxymethyl)benzoxazole-2-carboxylic acid.

EXAMPLE 38

5-(7-(4-(quinolin-2-ylmethyloxy)phenoxymethyl)benzoxazol-2-yl)tetrazole

Step 1: 7-bromomethyl-2-cyanobenzoxazole

When the 2-cyano-6-bromomethylbenzoxazole in Example 10, Step 2 is replaced with 2-cyano-7-methylbenzoxazole, 7-bromomethyl-2-cyanobenzoxazole is obtained.

Step 2:
2-cyano-6-(4-(quinolin-2-ylmethyloxy)phenoxymethyl)-benzoxazole 1.0 g of 4-(2-quinolinylmethyloxy)phenol, .9 g of 7-bromomethyl-2-cyanobenzoxazole and 0.5 g of potassium carbonate are stirred at room temperature in 5 ml of dimethylformamide for 2 days. The reaction mixture is diluted with ethylacetate, filtered and concentrated. The residue is chromatographed on silica gel to give 2-cyano-7-(4-(quinolin-2-ylmethyloxy)phenoxymethyl)-benzoxazole.

Step 3:
5-(7-(4-(quinolin-2-ylmethyloxy)phenoxymethyl)benzoxazol-2-yl)tetrazole

When the nitrile of Example 10, Step 4 is replaced with the cyano product from Example 37 above, 5-(7-

(4-(quinolin-2-ylmethyloxy)phenoxymethyl)benzoxazol-2-yl)-tetrazole is obtained.

EXAMPLE 39

6-(4-(quinolin-2-ylmethyloxy)phenoxymethyl)benzoxazole-2-carboxylic acid

Step 1: ethyl 6-(4-(quinolin-2-yl-methyloxy)phenoxymethyl)benzoxazole-2-carboxylate 0.8 g of 4-(2-quinolinylmethyloxy)phenol, 0.89 g of ethyl 6-bromomethylbenzoxazole-2-carboxylate and 0.44 g of potassium carbonate are combined in 15 ml of dimethylformamide and heated at 70° C. for 18 hours. The mixture is poured into water and the aqueous mixture extracted with ethyl acetate. The organic solution is dried and evaporated and the resulting crude product is purified by column chromatography on silica gel to give ethyl 6-(4-(quinolin-2-ylmethyloxy)phenoxymethyl)-benzoxazole-2carboxylate.

Step 2: 6-(4-(quinolin-2-ylmethyloxy)phenoxymethyl)benzoxazole-2-carboxylic acid When ethyl 6-(4-(quinolin-2-ylmethyloxy)phenoxymethyl)benzoxazole-2-carboxylate is substituted for the ester in Example 31, 6-(4-(quinolin-2-ylmethyloxy)-phenoxymethyl)benzoxazole-2-carboxylic acid is obtained.

EXAMPLE 40

5-(7-(4-(quinolin-2-ylmethyloxy)benzoylamino)benzoxazole-2-yl)tetrazole 5-(7-(3-(quinolin-2-ylmethyloxy)benzoylamino)benzoxazol-2-yl)tetrazole 5-(7-(2-(quinolin-2-ylmethyloxy)benzoylamino)benzoxazol-2-yl)tetrazole Step 1: 2-carbamyl-7-nitrobenzoxazole An excess of anhydrous ammonia gas is bubbled into a solution of 7.9 g of 2-carboethoxy-7-nitrobenzoxazole in 100 ml of ethanol and held at 0° C. for 20 minutes. This is stirred at 0° C. for 1 hour then concentrated in vacuo. The resulting oil is triturated with ether and the resulting precipitate filtered off giving 2-carbamyl-7-nitrobenzoxazole.

Step 2: 2-cyano-7-nitrobenzoxazole 26.14 g (17.22 mmoles) of phosphorus oxychloride is added to 100 ml dimethylformamide at 0° C. and stirred at 0° C. for 15 minutes at room temperature for 30 minutes. 6.5 g (34.45 mmoles) 2-carbamyl-7-nitrobenzoxazole is added and the mixture stirred at room temperature overnight, then poured into ice water and is allowed to stand for 1 hour at room temperature. The resulting precipitate is filtered off, redissolved in ethyl acetate, decolorized with carbon, filtered and the filtrate concentrated in vacuo to give 2-cyano-7-nitrobenzoxazole.

Step 3: 5-(7-nitrobenzoxazol-2-yl)tetrazole

When 2-cyano-7-nitrobenzoxazole is substituted for the cyano compound in Example 10, Step 4, then 5-(7-nitrobenzoxazol-2-yl)tetrazole is obtained.

Step 4: 5-(7-aminobenzoxazol-2-yl)tetrazole 1.59 g of the nitro compound obtained in Example 40, Step 3, above, is suspended in 46 ml of methanol to which 1 ml of concentrated hydrochloric acid, and 0.17 g of 5% palladium on carbon are added. The mixture is stirred under hydrogen at atmospheric pressure for 18 hours, filtered, and the filtrate concentrated in vacuo to obtain 5-(7-aminobenzoxazol-2-yl)tetrazole.

Step 5: 4-(quinolin-2-ylmethyloxy)benzoic acid 5.00 g of methyl-4-(quinolin-2-ylmethyloxy)benzoate is dissolved in 120 ml of ethanol and 90 ml of 1N sodium hydroxide and the mixture is stirred at room temperature for 4 days. The mixture is concentrated in vacuo to remove the ethanol. The residue is diluted with water, acidified to pH 6 and the resulting solid is filtered off and recrystallized from methanol to give 4-(quinolin-2ylmethyloxy)benzoic acid.

Step 6: 4-(quinolin-2-ylmethyloxy)benzoyl chloride 1.28 g of 4-(quinolin-2-ylmethyloxy)benzoic acid, in 4.6 ml of oxalyl chloride and 3 drops of dimethylformamide are combined in 50 ml of methylene chloride. The mixture is refluxed for 30 minutes and then concentrated in vacuo to give 4-(quinolin-2-ylmethyloxy)benzoyl chloride Step 7: 5-(7-(4-(quinolin-2-ylmethyloxy)benzoylamino)benzoxazol-2-yl)tetrazole 1.4 g of 4-(quinolin-2-ylmethyloxy)benzoyl chloride, as a solid, is added to a mixture of .92 g of 5-(7-aminobenzoxazol-2-yl)tetrazole, 14 ml of pyridine, 46 ml of methylene chloride and 30 ml of dimethylformamide at 0° C. This is stirred at 0° C. for 1 hour, then at room temperature for 2 days. The mixture is concentrated to remove methylene chloride and diluted with water. The resulting crude product is crystallized from methanol/ether to give 5-(7-(4-quinolin-2-ylmethyloxy)benzoylamino)benzoxazol-2-yl)tetrazole.

Step 8

When methyl-3-(quinolin-2-ylmethyloxy)benzoate or methyl-2-(quinolin-2-ylmethyloxy)benzoate is substituted for methyl-4-(quinolin-2-ylmethyloxy)benzoate in Example 39, Step 3, then 5-(7-(3-quinolin-2-ylmethyloxy)benzoylamino)benzoxazol-2-yl)tetrazole or 5-(7-(2-(quinolin-2-ylmethyloxy)benzoylamino)benzoxazol-2-yl)tetrazole, respectively, is obtained.

EXAMPLE 41

4-hydroxy-3-(4-methoxyphenyl)-6-(4-(quinolin-2-ylmethyloxy)benzoyloxy)-2,3-dihydrobenzoxazole-2-carboxylic acid Step 1 ethyl 4-hydroxy-3-(4-methoxyphenyl)-6-(4-(quinolin-2-ylmethyloxy)benzyloxy)-2,3-dihydrobenzoxazole-2-carboxylate 0.62 g of 4-(2-quinolinylmethyloxy)benzylchloride, 0.71 g of ethyl 4,6-dihydroxy-3-(4-methoxyphenyl)-2,3-dihydrobenzoxazole-2-carboxylate and 0.31 g potassium carbonate are refluxed in 30 ml of acetone for 17 hours. The mixture was concentrated and the crude product purified by flash chromatography on silica gel and crystallized from toluene to give ethyl 4-hydroxy-3-(4-methoxyphenyl)-6-(4-(quinolin-2-ylmethyloxy) benzyloxy)benzyloxy)-2,3-dihydrobenzoxazole-2-carboxylate.

Step 2:
4-hydroxy-3-(4-methoxyphenyl)-6-(4-quinolin-2-ylmethyloxy)benzyloxy)-2,3-dihydrobenzoxazole-2-carboxylic acid 0.11 g ethyl 4-hydroxy-3-(4-methoxyphenyl)-6-(4-(quinolin-2-ylmethyloxy)benzyloxy)-2,3-dihydrobenzoxazole-2-carboxylate and 0.78 g sodium bicarbonate are combined in 7 ml of water and 7 ml of ethanol and refluxed overnight. The mixture is extracted with ether and the aqueous neutralized to pH6. The resulting solid is collected, dried to give 4-hydroxy-3-(4-methoxyphenyl)-6-(4-(quinolin-2-ylmethyloxy)benzyloxy)-2,3-dihydrobenzoxazole-2-carboxylic acid.

EXAMPLE 42

3-(6-(3-(quinolin-2-ylmethyloxy)benzyloxy)-2.3-dihydro-3-methylbenzoxazol-2-yl)propanoic acid Step 1:
ethyl-3-(6-(3-(quinolin-2-ylmethyloxy)-benzyloxy)-2,3-dihydro-3-methylbenzoxazol-2-yl)-propanoate 2.0 g of ethyl-3-(2,3-dihydro-6-hydroxy-2-methylbenzoxazol-2-yl)propanoate, 3.1 g of 2-(3-chloromethylphenoxy)methylquinoline and 1.2 g potassium carbonate are combined in 25 ml of dimethylformamide and stirred at room temperature overnight, then at 60° C. for 4 hours. The reaction mixture is diluted with ethyl acetate and this solution washed with water, dried and concentrated. The residue is chromatographed on silica gel to give ethyl-3-(6-(3-(quinolin-2-ylmethyloxy)-benzyloxy)-2,3-dihydro -2-methylbenzoxazol-2-yl)propanoate which is used, without further purification, for the next step.

Step 2:
3-(6-(3-(quinolin-2-ylmethyloxy)benzyloxy)-2,3-dihydro-3-methylbenzoxazol-2-yl)propanoic acid.

2.1 g of ethyl-3-(6-(3-(quinolin-2-ylmethyloxy)-benzyloxy)-2,3-dihydro-3-methylbenzoxazol-2s -yl)-propanoate and 1.02 g of lithium hydroxide hydrate are combined in 30 ml of methanol, 30 ml of tetrahydrofuran and 20 ml of water and stirred at room temperature for 3 hours. The solvent is removed by evaporation and the residue diluted with water and washed with ether. The pH of the aqueous portion is adjusted to 5 and the suspension extracted with ethyl acetate. The dried ethyl acetate solution is concentrated and the residue purified by chromatography on silica gel to give 3-(6-(3-(quinolin-2-ylmethyloxy)-benzyloxy)-2,3-dihydro-3-methylbenzoxazol-2-yl) propanoic acid.

EXAMPLE 43

(E)-5-(6-[3-(7-chloro-2-quinolinylethenyl)phenoxymethyl]-benzoxazol-2-yl)tetrazole Step 1: (E)-3-(7-chloro-2-quinolinylethenyl)phenyl acetate A solution of 7-chloroquinaldine (10 g, 56.3 mmol) and 3-hydroxybenzaldehyde (6.87 g, 56.3 mmol) in 25 ml of acetic anhydride is heated at 130° C. for 16 hours. The reaction mixture is concentrated and the beige solid recrystallized from hexane-ethyl acetate to afford (E)-3-(7-chloro-2-quinolinylethenyl)phenyl acetate which is used directly in the next step.

Step 2: (E)-3-(7-chloro-2-quinolinylethenyl)phenol

A mixture of (E)-3-(7-chloro-2-quinolinylethenyl)-phenyl acetate (7.4 g, 22.9 mmol) and anhydrous sodium carbonate (606 mg, 5.7 mmol) in 135 ml of methanol is stirred at room temperature for 36 hours. pH 7 buffer (250 ml) is added and the precipitated solid filtered and dried to afford (E)-3-(7-chloro-2-quinolinylethenyl)-phenol which is used directly in the next step.

Step 3:
(E)-2-cyano-6-[3-(7-chloro-2-quinolinylethenyl)-phenoxymethyl]benzoxazole To a stirred solution of the (E)-3-(7-chloro-2quinolinylethenyl)phenol (1.485 g, 5.28 mmol) in acetone (120 ml) and dimethylformamide (15 ml) at room temperature are added successively potassium carbonate (1.09 g, 7.0 mmol) and 2-cyano-6-(bromomethyl)-benzoxazole (1.25 g, 5.27 mmol). The resulting solution-suspension is refluxed for 16 hours and concentrated. Water (100 ml) and ethyl acetate (150 ml) are added. Extraction with ethyl acetate is followed by washing with water and brine, drying (MgSO₄) and evaporation under reduced pressure. The residue is subjected to flash chromatography over silica gel. Elution is with 33% ethyl acetate in hexane and concentration of the appropriate fractions provides (E)-2-cyano-6-[3-(7-chloro-2-quinolinylethenyl) phenoxymethyl]-benzoxazole.

Step 4:
(E)-5-(6-[3-(7-chloro-2-quinolinylethenyl)phenoxymethyl-]benzoxazol-2-yl)tetrazole A solution-suspension of (E)-2-cyano-6-[3-(7-chloro-2-quinolinylethenyl)phenoxymethyl]benzoxazole (950 mg, 2.17 mmol), sodium azide (432.1 mg, 6.51 mmol) and ammonium chloride (348.1 mg, 6.51 mmol) in DMF (15 ml) is heated to 100° C. for 7 hours and stirred at room temperature for 12 hours. The mixture is poured over ice-water and the pH is adjusted to 10 with 1N NaOH. The aqueous mixture is washed with ether and the pH adjusted to 4 with 1N-HCl. The precipitated solid is filtered and washed successively with water, ethanol and methylene chloride. Recrystallization from DMF affords (E)-5-(6-[3-(7-chloro-2-quinolinylethenyl)phenoxymethyl ]benzoxazol-2-yl)tetrazole. (M.P. 272° C. (dec.))

EXAMPLE 44

When 3-hydroxybenzaldehyde is replaced in Example 43, Step 1 with 4-hydroxybenzaldehyde then the product prepared is (E)-5-(6-[4-(7-chloro-2-quinolinylethenyl)phenoxymethyl]benzoxazol-2-yl)tetrazole (M.P. 236–279° C. (dec.)).

EXAMPLE 45

When (E)-2-cyano-6-(bromomethyl)benzoxazole in Example 43, Step 3 is replaced with (E)-2-cyano-5-(bromomethyl)benzoxazole then the compound prepared is (E)-5-(5-[3-(7-chloro-2-quinolinylethenyl)-phenoxymethyl]benzoxazol-2-yl) tetrazole.

EXAMPLE 46

When (E)-2-cyano-6-(bromomethyl)benzoxazole in Example 43, Step 3 is replaced with (E)-2-cyano-3-methyl-5-(bromo-methyl)benzo(b)thiophene or 3-methyl-5-(bromomethyl)benzo(b)thiophene-2-carboxylic acid then the products prepared are 5-(5-[3-(7-chloro-2-quinolinylethenyl)phenoxymethyl]3-methylbenzo(b)-thiophene -2 -yl)tetrazole and 5-[3-(7-chloro-2- quinolinylethenyl)phenoxymethyl]-3-methylbenzo(b)-thiophene-2-carboxylic acid.

EXAMPLE 47

When 3-hydroxybenzaldehyde is replaced in Example 43, Step 1 with 4-hydroxybenzaldehyde and (E)-2-cyano-6-(bromomethyl)benzoxazole is replaced in step 3 with (E)-2-cyano-5-(bromomethyl)benzo(b)thiophene or 5-(bromomethyl)benzo(b)thiophene-2-carboxylic acid then the products prepared are 5-(5-[4-(7-chloro-2-quinolinylethenyl)-phenoxymethyl]-benzo(b)thiophene-2-yl)tetrazole and 5-[4-(7-chloro-2-quinolinylethenyl)phenoxymethyl]benzo(b)-thiophene-2-carboxylic acid.

EXAMPLE 48

3-methyl-5-[3-(2-quinolinylmethyloxy)-benzyloxy]benzo(b)thiophene-2-carboxylic acid

Step 1: Methyl 5-hydroxy-3-methylbenzo(b)thiophene-2carboxylate

Dry HCl gas is bubbled through a solution of 5-hydroxy-3-methylbenzo(b)thiophene-2-carboxylic acid (1.0 g, 4.81 mmol) in methanol (150 ml) for 1 hour at room temperature. The brown solution is refluxed for 2 hours and concentrated. Extraction with ether, washing with water, aqueous sodium bicarbonate, water and bring, drying (MgSO₄) and concentration affords the crude product which is subjected to flash chromatography over silica gel. Elution with 33% ethyl acetate in hexane affords methyl 5-hydroxy-3-methylbenzo(b)thiophene-2-carboxylate.

Step 2: Methyl-3-methyl-5-[3-(2-quinolinyl-methyloxy)benzyloxy)-benzo(b)thiophene-2-carboxylate To a stirred solution of methyl 5-hydroxy-3-methylbenzo(b)thiophene-2-carboxylate (878.6 mg, 3.96 mmol) in dry DMF (20 ml) at room temperature is added sodium hydride (158 mg, 3.95 mmol) as a 60% dispersion in mineral oil. After 30 minutes of stirring 3-(2-quinolinylmethoxy)benzyl chloride (1.02 g, 3.60 mmol) is added. The solution is stirred at room temperature for 4 hours and quenched with ice-water. Extraction with ethyl acetate, washing with aqueous sodium carbonate, water and brine is followed by drying (MgSO₄) and concentration. The residue is subjected to flash chromatography on silica gel. Elution with 25% ether in hexane affords methyl-3-methyl-5-[3-(2-quinolinylmethoxy)benzyloxy]benzo(b) -thiophene-2-carboxylate.

Step 3: 3-methyl 5-[3-(2-quinolinylmethyloxy)benzyloxy]-benzo(b)thiophene-2-carboxylic acid.

To a stirred solution of methyl-3-methyl-5-[3-(2quinolinylmethyloxy)benzyloxy]benzo(b)thiophene-2-carboxylate (355 mg, 0.76 mmol) in THF (10 ml), methanol (10 ml) and water (10 ml) at room temperature is added lithium hydroxide monohydrate (156 mg, 3.71 mmol). The resulting solution is stirred for 16 hours and concentrated. The residue is suspended in water and washed with ether. The aqueous layer is acidified to pH 3. The precipitated solid is filtered, washed with water and methylene chloride and dried to provide 3-methyl 5-[3(2-quinolinylmethyloxy)-benzyloxy]benzo(b)thiophene -2-carboxylic acid.

EXAMPLE 49

When 5-hydroxy-3-methylbenzo(b)thiophene-2-carboxylic acid in Example 48, Step 1 is replaced with 5-hydroxy-benzo(b)thiophene-2-carboxylic acid then the compounds prepared are: methyl-5-[3-(2-quinolinylmethyloxy)benzyloxy]benzo(b)thiophene-2-carboxylate (M.P. 114–115° C.) and 5-[3-(2-quinolinylmethyloxy)benzyloxy]benzo(b)-thiophene-2-carboxylic acid (M.P. 194–196° C.).

EXAMPLE 50

When 3-(2-quinolinylmethyloxy)benzyl chloride in Example 48, Step 2 is replaced with 4-(2-quinolinylmethyloxy)benzyl chloride then the products prepared are methyl-3-methyl-5-[4-(2-quinolinylmethyloxy)benzyloxy]benzo(b)thiophene-2-carboxylate and 3-methyl-5-[4-(2-quinolinylmethyloxy)benzyloxy]benzo(b)thiophene-2carboxylic acid (M.P. 118–121° C.).

EXAMPLE 51

When 5-hydroxy-3-methylbenzo(b)thiophene-2-carboxylic acid of Example 48, Step 1 is replaced with 5-hydroxybenzo(b)thiophene-2-carboxylic acid and 3-(2-quinolinylmethyloxy)benzyl chloride of Step 2 is replaced with 4-(2-quinolinylmethyloxy)benzyl chloride then the products prepared are methyl-5-[4-(2-quinolinylmethyloxy)benzyloxy]benzo(b)thiophene-2-carboxylate and 5-[4-(2-quinolinylmethyloxy)-benzyloxy]benzo(b)thiophene-2carboxylic acid.

EXAMPLE 52

5-(5-[3-(2-quinolinylmethyloxy)benzyloxy]-3methyl-benzo(b)thiophen-2-yl)tetrazole

Step 1: 5-[3-(2-quinolinylmethyloxy)benzyloxy-]3-methylbenzo(b)thiophene-2-carboxamide To a stirred solution of 2-carboxy-3-methyl-5-[3-(2quinolinylmethyloxy)benzyloxy]benzo(b)thiophene (300 mg, 0.77 mmol) in DMSO (5 ml) at room temperature is added 1,1'-carbonyldiimidazole (150 mg, 0.92 mmol). The resulting solution is stirred at 60° C. for 1 hour, cooled to room temperature and gaseous ammonia bubbled through it for 35 minutes. Aqueous ammonium hydroxide (28%, 1 ml) is added and the solution-suspension stirred for 16 hours. Water and methylene chloride are added. The precipitated solid is filtered, washed with copious amounts of water and methylene chloride and dried to afford 5-(5-[3-(2-quinolinylmethyloxy)benzyloxy]-3-methylbenzo(b)thiophen -2-yl)tetrazole (M.P. 194–195° C.).

Step 2: 2-cyano-5-[3-(2-quinolinylmethyloxy)benzyloxy]-3-methylbenzo(b)thiophene To a stirred solution of 5-[3-(2-quinolinylmethyloxy)-benzyloxy]-3-methylbenzo(b)thiophene-2-carboxamide (454.5 mg, 1 mmol) in pyridine (10 ml) at room temperature is added methanesulfonyl chloride (387 μL, 5 mmol). The solution is stirred for 16 hours and water (50 ml) and ethyl acetate (100 ml) are added. Extraction with ethyl acetate, washing with water and brine, drying (MgSO₄) and concentration affords a crude product which is chromatographed over silica gel. Elution with 25% ethyl acetate in hexane provides 2-cyano-5-[3-(2-quinolinylmethyloxy)benzyloxy]-3-methylbenzo(b)thiophene.

Step 3:
5-(5-[3-(2-quinolinylmethyloxy)benzyloxy]-3-methylbenzo(b)thiophen-2-yl)tetrazole A solution-suspension of 2-cyano-5-[3-(2-quinolinylmethyloxy)benzyloxy]-3-methylbenzo(b)thiophene (300 mg, 0.69 mmol), sodium azide (134 mg, 2.1 mmol) and ammonium chloride (110.3 mg, 2.1 mmol) in DMF (3 ml) is heated to 80° C. for 16 hours. The reaction mixture is cooled to room temperature and poured over ice-water. The pH is adjusted to 10 (1N NaOH) and the aqueous layer washed with ether and then acidified to pH 3. The precipitated solid is filtered and washed successively with water, ethanol and methylene chloride and dried to afford 5-(5-[3-(2quinolinylmethyloxy)-benzyloxy]-3-methylbenzo(b)thiophen -2-yl)tetrazole (M.P. 195–196° C. (dec)).

EXAMPLE 53

When 3-methyl-5-[3-(2-quinolinylmethyloxy)benzyloxy]benzo(b)thiophene-2-carboxylic acid of Example 52, Step 1 is replaced with 3-methyl-5-[4-(2-quinolinylmethyloxy)benzyloxy]benzo(b)thiophene -2-carboxylic acid then the products prepared are 5-[4-(2-quinolinylmethyloxy)benzyloxy]-3-methylbenzo(b)thiophene-2carboxamide (M.P. 224–225° C.), 2-cyano-5-[4-(2-quinolinylmethyloxy)benzyloxy]-3-methyl-benzo(b)thiophene (M.P. 159–160° C.) and 5-(5-[4-(2-quinolinylmethyloxy)benzyloxy]-3-methylbenzo(b)thiophen-2-yl)tetrazole (M.P. 193–195° C. (dec)).

EXAMPLE 54

When 3-methyl-5-[3-(2-quinolinylmethyloxy)benzyloxy]-benzo(b)thiophene-2-carboxylic acid of Example 52, Step 1 is replaced with 5-[4-(2-quinolinylmethyloxy)benzyloxy]-benzo(b)thiophene-2-carboxylic acid then the products prepared are 5-[4-(2-quinolinylmethyloxy)benzyloxy]-benzo(b)thiophene-2-carboxamide, 2-cyano-5-[4-(2-quinolinylmethyloxy)-benzyloxy]benzo(b)thiophene and 5-(5-[4-(2-quinolinylmethyloxy)benzyloxy]benzo(b)thiophen-2yl)tetrazole.

EXAMPLE 55

N-1H-(5-tetrazolyl)-5-[3-(2-quinolinylmethyloxy)benzyloxy]-3-methylbenzo(b)thiophene -2-carboxamide To a stirred solution of 3-methyl-5-[3-(2-quinolinylmethyloxy)benzyloxy]benzo(b)thiophene-2-carboxylic acid (250 mg, 0.55 mmol) in DMSO (6 ml) at room temperature is added 1,1'-carboxyldiimidazole (178 mg, 1.10 mmol) and the resulting solution is stirred at 60° C. for 1 hour. Triethylamine (153 μL, 1.10 mmol) and 5-aminotetrazole monohydrate (113.2 mg, 1.10 mmol) are added successively and the solution stirred at 60° C. for 16 hours. The reaction mixture is cooled to room temperature and poured over ice-water. The pH is adjusted to 10 and the aqueous layer washed with ether. The pH is then adjusted to 3 and the precipitated material obtained by filtration and washing successively with water, ethanol and methylene chloride. Further drying under vacuum affords N-1H-(5-tetrazolyl)-5-[3-(2-quinolinylmethyloxy)benzyloxy ]-3-methylbenzo(b)thiophene-2-carboxamide (M.P. 220–224° C. (dec)).

EXAMPLE 56

When 3-methyl-5-[3-(2-quinolinylmethyloxy)benzyloxy)-benzo(b)thiophene-2-carboxylic acid of Example 55 is replaced by the acids of Examples 49, 50 and 51 then the products prepared are N-1H-(5-tetrazolyl)-5-[3-(2-quinolinylmethyloxy)benzyloxy]benzo(b)thiophene -2carboxamide; N-1H-(5-tetrazolyl)-5-[4-(2-quinolinylmethyloxy)benzyloxy]benzo(b)thiophene-2-carboxamide (M.P. 236–238° C. (dec)) and N-1H-(5-tetrazolyl)-5-[4-(2-quinolinylmethyloxy)benzyloxy ]-3-methylbenzo(b)thiophene-2carboxamide.

EXAMPLE 57

When 2-cyano-6-methylbenzoxazole in Example 10, Step 2 and Example 16 is replaced by the compounds of Table IV below, the corresponding products may be prepared.

TABLE IV 2-cyano-5-methylbenzofuran
2-cyano-5-methyl-1H-indole
2-cyano-5-methyl-1,3-benzoxathiole
3-cyano-6-methyl-1H-indazole
2-cyano-5-methyl-1H-benzimidazole
2-cyano-6-methylbenzothiazole
3-cyano-5-methyl-1,2-benzisothiazole
2-cyano-5-methyl-1,3-benzodithiole
3-cyano-6-methyl-1,2-benzisoxazole
3-cyano-5-methylbenzoxazole

EXAMPLE 58

When 5-hydroxybenzoxazole-2-carboxylic acid in Example 29 is replaced by the compounds of Table V below, then the corresponding products are prepared.

TABLE V 2-carboxy-5-hydroxybenzofuran
2-carboxy-5-hydroxy-1H-indole
2-carboxy-5-hydroxy-1,3-benzoxathiole
3-carboxy-6-hydroxy-1H-indazole
2-carboxy-5-hydroxy-1H-benzimidazole
2-carboxy-6-hydroxybenzothiazole
3-carboxy-5-hydroxy-1,2-benzisothiazole
2-carboxy-5-hydroxy-1,3-benzodithiole
3-carboxy-6-hydroxy-1,2-benzisoxazole
3-carboxy-5-hydroxybenzoxazole

EXAMPLE 59

When the products obtained from Examples 5 and 6 are substituted for 2-(4-hydroxyphenoxy)methylquinoline in Example 36, Step 2, the corresponding product is obtained.

EXAMPLE 60

When the compounds from Table VI below, are substituted for 6-bromomethyl-2-carboethoxybenzoxazole in Example 59, the corresponding product is obtained.

TABLE VI 4-bromomethyl-2-carboethoxybenzoxazole
5-bromomethyl-2-carboethoxybenzoxazole
7-bromomethyl-2-carboethoxybenzoxazole

EXAMPLE 61

Ethyl-6-(4-(quinolin-2-ylmethyloxy)-phenylsulfinylmethyl)benzoxazole-2-carboxylate When ethyl-6-(4-(quinolin-2-ylmethyloxy)phenylthiomethyl)benzoxazole-2-carboxylic acid (from Example 59) is treated with one equivalent of m-chloroperbenzoic acid in methylene chloride, ethyl-6-(4-(quinolin-2-ylmethyloxy)-phenylsulfinylmethyl)benzoxazole-2-carboxylate is obtained.

EXAMPLE 62 ethyl-6-(4-(quinolin-2-ylmethyloxy)-phenylsulfonylmethyl)benzoxazole-2-carboxylate When the sulfoxide obtained in Example 61 is treated with an excess of m-chloroperbenzoic acid in methylene chloride, ethyl-6-(4-(quinolin-2-ylmethyloxy)phenylsulfonylmethyl)benzoxazole-2-carboxylate is obtained.

EXAMPLE 63

3-(4-(2-cyanobenzoxazol-6-ylmethoxymethyl)-4-(quinolin-2-ylmethyloxy)phenoxy)propanoic acid

Step 1:
2-(4-benzoyloxy-3-hydroxymethylphenoxy)methylquinoline

When 2-benzoyloxy-5-hydroxybenzyl aclohol is substituted for the alcohol in Example 7, then 2-(4-benzyloxy-3-hydroxymethylphenoxy)methylquinoline is obtained.

Step 2:
2-(2-benzoyloxy-5-chloromethyl)methylquinoline

When 2-(4-benzoyloxy-3-hydroxymethylphenoxy)methylquinoline is substituted for the quinoline in Example 10, then 2-(4-benzoyloxy-3-chloromethylphenoxy)methylquinoline is obtained.

Step 3
2-cyano-6-(2-benzoyloxy-5-(quinolin-2ylmethyloxy)-benzyloxy)benzoxazole When 2-(2-benzoyloxy-5-chloromethyl)methylquinoline is substituted for the quinoline in Example 25, 2-cyano-6-(4-benzoyloxy-3-(quinolin-2-ylmethyloxy)benzyloxy) benzoxazole is obtained.

Step 4:
2-cyano-6-(2-hydroxy-5-(quinolin-2-ylmethyloxy)benzyloxy)benzoxazole When the ester from Example 63 Step 3, above, is substituted for the ester in Example 31, 2-cyano-6-(2-hydroxy-5-(quinolin-2-ylmethyloxy)benzyloxy)benzoxazole is obtained.

Step 5: ethyl 3-(2-(2-cyanobenzoxazol-6-ylmethoxy-methyl)-4-(quinolin-2-ylmethyloxy)phenoxy) propanoate The hydroxy compound from Example 63 Step 4, above, is treated with ethyl-3-bromoproprionate in dimethylformamide in the presence of potassium carbonate. The mixture is poured into water, extracted with ethyl acetate and the ethyl acetate solution washed with water, dried, evaporated to give ethyl 3-(2-(2-cyanobenzoxazol-6-ylmethoxymethyl)-4-(quinolin-2-ylmethyloxy)phenoxy) propanoate.

Step 6:
3-(2-(2-cyanobenzoxazol-6-yl-methoxymethyl)-4-(quinolin-2-ylmethyloxy)phenoxy)propanoic acid When the above ester is substituted for the ester in Example 31, 3-(2-(2-cyanobenzoxazol-6-ylmethyloxymethyl)-4-(quinolin-2-ylmethyloxy)phenoxy)-propanoic acid is obtained.

EXAMPLE 63A 5-(3-(2-(2-tetrazol-5-ylbenzoxazol-6-ylmethoxymethyl)-4-(quinolin-2-ylmethyloxy)phenoxy) propyl)tetrazole

Step 1: ethyl 3-(2-(2-tetrazol-5-ylbenzoxazol-6-yl-methoxymethyl)-4-(quinolin -2-ylmethyloxy)phenoxy)-propanoate When the cyano compound obtained in Example 63, Step 5, above, is substituted for the cyano compound in Example 17, ethyl 3-(2-(2-tetrazol-5-ylbenzoxazol-6-ylmethyloxy-methyl)-4-(quinolin-2-ylmethyloxy) phenoxy)propanoate is obtained.

Step 2:
3-(2-(2-tetrazol-5-ylbenzoxazol-6-ylmethoxy-methyl)-4-(quinolin-2-ylmethyloxy) phenoxypropanamide When the ester obtained in Example 63A, Step 1, above, is substituted for the ester in Example 40, Step 1, 3-(2-(2-tetrazol-5-ylbenzoxazol-6-ylmethoxymethyl)-4-(quinolin-2-yl-methyloxy)phenoxy)propanamide is obtained.

Step 3:
3-(2-(2-tetrazol-5-ylbenzoxazol-6-ylmethoxy-methyl)-4-(quinolin-2-ylmethyloxy)phenoxy) propanonitrile When the amide obtained in Example 63A, Step 2, above, is substituted for the amide in Example 40, Step 2, 3-(2-(2-tetrazol-5-ylbenzoxazol-6-ylmethoxymethyl)-4-(quinolin-2-yl-methyloxy)phenoxy)propanonitrile is obtained.

Step 4:
5-(3-(2-(2-tetrazol-5-ylbenzoxazol-6-ylmethoxymethyl)-4-(quinolin-2-ylmethyloxy) phenoxy)propyl)tetrazole When the cyano compound obtained in Example 63A, Step 3, above, is substituted for the cyano compound in Example 40, Step 3, 5-(-3-(2-(2-tetrazol-5-ylbenzoxazol-6-ylmethoxymethyl) -4-(quinolin-2-ylmethyloxy)phenoxy)-propyl)tetrazole is obtained.

EXAMPLE 64

2-cyano-5-(1-hydroxy-2-((2-carboxyethyl)thio)-2-(3-quinolin-2-ylmethyloxy)phenyl) ethylbenzoxazole

Step 1:
2-cyano-5-(1,2-oxido-2(3-(quinolin-2-ylmethyloxy)-phenyl)ethyl)benzoxazole To a solution of 0.1 mole of 2-cyano-5-(2-(3-quinolin-2-ylmethyloxy)phenyl)ethenyl)benzoxazole in 300 ml of methylene chloride containing 5 g of sodium bicarbonate, at 10° C., is added 0.11 mole of m-chloroperbenzoic acid. The mixture is stirred at 10° C. for several hours, then at room temperature. The solution is filtered, the methylene chloride washed with sodium bisulfite solution, potassium carbonate solution, then dried and evaporated in vacuo to give 2-cyano-5-(1,2-oxido-2-(3-(quinolin-2-ylmethyloxy)phenyl)ethyl) benzoxazole.

Step 2:
2-cyano-5-(1-hydroxy-2-((2-carbomethoxyethyl)-thio)-2-(3-(quinolin-2-ylmethyloxy) phenyl)ethyl)-benzoxazole 0.08 mole of the epoxide obtained in Example 64, Step 1, above, is stirred with 0.08 mole of methyl 3-thiolpropionate in 300 ml of methylene chloride at room temperature. The solvent is removed in vacuo and a mixture of the two isomers, 2-cyano-5-(1-hydroxy-2-((2-carbomethoxyethyl)thio)-2-(3-(quinolin-2-ylmethyloxy)-phenyl)ethyl)benzoxazole and 2-cyano-5-(2-hydroxy-1-((2-carbomethoxyethyl)thio-2-(3-(quinolin-2-ylmethyloxy)phenyl) ethyl)benzoxazole, is obtained. The isomers are separated by flash chromatography.

Step 3:
2-cyano-5-(1-hydroxy-2-((2-carboxyethyl)thio)-2-(3-(quinolin-2-ylmethyloxy)phenyl) ethyl)benzoxazole When the 1-hydroxy ester obtained in Example 64, Step 2, above, is substituted for the ester in Example 31, 1-cyano-5-(1-hydroxy-2-((2-carboxyethyl)thio) -2-(3-quinolin-2-yl-methyloxy)phenyl)ethyl)benzoxazole is obtained.

EXAMPLE 65

2-cyano-5-(2-hydroxy-1-((2-carboxyethyl)thio)-2-(3-quinolin-2-ylmethyloxy)phenyl)ethyl) benzoxazole When the remaining isomer of the ester obtained in Example 64, Step 2, is substituted for the ester in Example 64, Step 3, 2-cyano-5-(2-hydroxy-1-((2-carboxyethyl)thio)-2-(3-quinolin-2-ylmethyloxy)phenyl)ethyl)-benzoxazole is obtained.

EXAMPLE 66

When the products obtained in Example 20 are substituted for the ethenyl compound in Example 64, Step 1, the corresponding products are obtained.

EXAMPLE 67

5-((6-(4-(quinolin-2-ylmethyloxy)phenoxymethyl)-benzoxazol-2-yl)methyl)tetrazole

Step 1: methyl 2-(6-bromomethylbenzoxazol-2-yl)acetate

When methyl-2-(6-methylbenzoxazol-2-yl)acetate is substituted for the ester in Example 10, Step 2, methyl 2-(6-bromomethylbenzoxazol-2-yl)acetate is obtained.

Step 2: methyl 2-(6-(4-(quinolin-2-ylmethyloxy)phenoxy-methyl)benzoxazol-2-yl)acetate When the bromomethyl product from Example 67, Step 1, is substituted for the bromomethyl compound in Example 36, Step 2, methyl 2-(6-((4-quinolin-2-ylmethyloxy)phenoxy-methyl)benzoxazol-2-yl)acetate is obtained.

Step 3: 2-(6-(4-(quinolin-2-ylmethyloxy)phenoxymethyl)-benzoxazol-2-yl)acetamide When the ester in Example 40, Step 1, is replaced by the ester obtained in Example 67, Step 2, 2-(6-(4-(quinolin-2-yl-methyloxy)phenoxymethyl)benzoxazol-2yl) acetamide is obtained.

Step 4: 2-(6-(4-(quinolin-2-ylmethyloxy)phenoxymethyl)-benzoxazol-2-yl)acetonitrile When the amide in Example 40, Step 2 is replaced by the amide obtained in Example 67, Step 3, 2-(6-(4-(quinolin-2-ylmethyloxy)phenoxymethyl)benzoxazol-2-yl)acetonitrile is obtained.

Step 5:
5-((6-(4-(quinolin-2-ylmethyloxy)phenoxymethyl)-benzoxazol-2-yl)methyl)tetrazole When the nitrile in Example 10, Step 4 is replaced by the nitrile obtained in Example 67, Step 4, 5-((6-(4-(quinolin-2-ylmethyloxy)phenoxymethyl)benzoxazol-2yl) methyl)tetrazole is obtained.

We claim:
1. A compound of the formula:

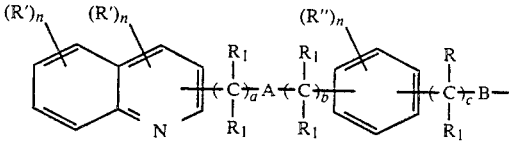

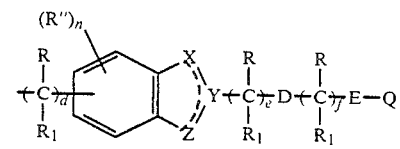

where:
A is O, S,

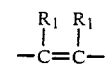

or a carbon-carbon single bond;
B is a carbon-carbon single bond, O, S, SO, $SO_2$, $NR_1$,

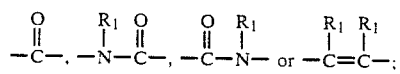

D is O, S, $NR_1$,

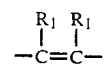

or a carbon-carbon single bond;
E is a carbon-carbon single bond or

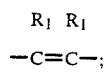

a is 0–1; b is 0–1; c is 0–3; d is 0–3; e is 0–3; f is 0–3; n is 0–2;
X is $NR_2$, O or S;
Y is $CR_2R_3$ or $NR_2$ when Z is $CR_2R_3$;
Z is $CR_2R_3$, $NR_2$, O or S;
R' is independently hydrogen, alkyl, hydroxy, alkoxy, carboxy, carbalkoxy, halo, nitro, haloalkyl, cyano or acyl;
R" is independently hydrogen, hydroxy, alkoxy, halo, haloalkyl, or —$(CH_2)_x$—F—$(CH_2)_y$—G;
$R_1$ is independently hydrogen, alkyl or aralkyl;
$R_2$ is a bond, hydrogen or alkyl;
$R_3$ is hydrogen or together with a vicinal $R_3$ group a double bond;
R is independently hydrogen or —$(CH_2)_x$—F—$(CH_2)_y$—G provided F and A or B are not geminal oxygen atoms;
x is 0–3; y is 0–3;

F is a carbon-carbon single bond, O, S or NR₁;
G is hydrogen, alkyl, alkenyl, cycloalkyl, aryl, aralkyl, hydroxy, alkoxy, aralkoxy, amino, mono- and di-alkylamino, aralkylamino, acylamino, —CONR₁R₁, —COOR, CN, tetrazolyl,

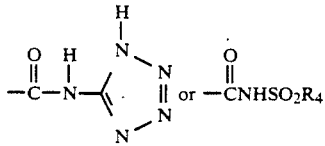

where R₄ is hydrogen, alkyl haloalkyl, phenyl or benzyl;

vicinal R groups together may be (CH₂)ᵧ—where y is 1–4, thus forming a 3–6 membered ring;

geminal R₁ and R₁ groups may together form a spiro substituent, —(CH₂)ᵤ—, where z is 2–5;

geminal R₁ or R₁ and R groups may together form an alkylidenyl substitutent,

Q is —COOR₁,—CN,

where R₄ is as described above,

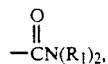

—OR₁, tetrazolyl, substituted tetrazolyl where the substituent may be alkyl, carboxyalkyl or carbalkoxyalkyl or

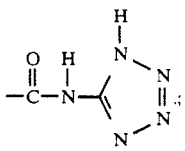

or a pharmaceutically acceptable salt thereof.

2. A compound of claim 1 where: one of R is —(CH₂)ₓ—F—(CH₂)ᵧ—G, —S—(CH₂)ₓ—G or —NR₁-(CH₂)ₓ—G; and/or one of R" is —CH₂R, R or —CH₂-O-(CH₂)ₓ—G and G is —CONR₁R₁, —COOR₁, —CN, tetrazolyl,

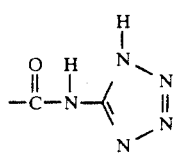

or acylsulfonamido.

3. A compound of claim 2 where: B is O, S,

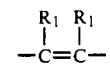

or a carbon-carbon single bond; Q is —COOR₁, —CON(R₁)₂, tetrazolyl or

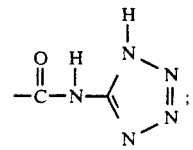

and R and R" are as described above.

4. A compound of claim 1 which is 5-(6-(3-(2-quinolinyl-methyloxy)phenoxymethyl)benzoxazol-2-yl)tetrazole.

5. A compound of claim 1 which is 5-(6-(4-(2-quinolinyl-methyloxy)phenoxymethyl)benzoxazol-2-yl)tetrazole.

6. A compound of claim 1 which is 2-ethoxyethyl-6-[3-(2quinolinylmethyloxy)phenoxymethyl]benzoxazole-2carboxylate.

7. A compound of claim 1 which is trans-(E)-5-(6-(2-(3-quinolin-2-ylmethyloxy)phenyl)ethenyl)benzoxazol-2-yl)tetrazole.

8. A compound of claim 1 which is 5-(6-(2-(3-(quinolin-2-ylmethyloxy)phenyl)ethyl)benzoxazol-2-yl) tetrazole.

9. A compound of claim 1 which is 5-(6-(3-(quinolin-2-ylmethyloxy)benzyloxy)benzoxazol-2-yl)tetrazole.

10. A compound of claim 1 which is n-propyl-5-(3-(quinolin-2-ylmethyloxy)benzyloxy)benzoxazole-2carboxylate.

11. A compound of claim 1 which is 5-(3-(quinolin-2-ylmethyloxy)benzyloxy)benzoxazole-2-carboxylic acid.

12. A compound of claim 1 which is ethyl-6-(3-(quinolin-2-ylmethyloxy)benzyloxy)benzoxazole-2-carboxylate.

13. A compound of claim 1 which is 5-(7-(quinolin-2-ylmethyloxy)phenoxymethyl)benzoxazol-2-yl)tetrazole.

14. A compound of claim 1 which is 6-(4-(quinolin-2-ylmethyloxy)phenoxymethyl)benzoxazole-2-carboxylic acid.

15. A compound of claim 1 which is (E)-5-(6-[3-(7-chloro-2-quinolinylethenyl)phenoxymethyl)benzoxazol -2yl)tetrazole.

16. A compound of claim 1 which is 5-(6-[4-(7-chloro-2quinolinylethenyl)phenoxymethyl]benzoxazol-2-yl)tetrazole.

17. A compound of claim 1 which is 5-(5-[3-(7-chloro-2-quinolinylethenyl)phenoxymethyl]benzoxazol-2-yl)tetrazole.

18. A compound of claim 1 which is 5-[3-(7-chloro-2quinolinylethenyl)phenoxymethyl]-3-methylbenzo(b)-thiophene-2-carboxylic acid.

19. A compound of claim 1 which is 5-[4-(7-chloro-2quinolinylethenyl)phenoxymethyl]benzo(b)thiophene-2carboxylic acid.

20. A compound of claim 1 which is 3-methyl-5-[3-(2quinolinylmethyloxy)benzyloxy]benzo(b)thiophene-2carboxylic acid.

21. A compound of claim 1 which is 5-[3-(2-quinolinylmethyloxy)benzyloxy]benzo(b)thiophene-2-carboxylic acid.

22. A compound of claim 1 which is 3-methyl-5-[4-(2quinolinylmethyloxy)benzyloxy]benzo(b)thiophene-2carboxylic acid.

23. A compound of claim 1 which is 5-[4-(2-quinolinylmethyloxy)benzyloxy]benzo(b)thiophene-2-carboxylic acid.

24. A compound of claim 1 which is 5-(5-[3-(2-quinolinylmethyloxy)benzyloxy]-3-methylbenzo(b)thiophen-2-yl)tetrazole.

25. A compound of claim 1 which is 5-(5-[4-(2-quinolinylmethyloxy)benzyloxy]-3-methylbenzo(b)thiophen-2-yl)tetrazole.

26. A compound of claim 1 which is 5-(5-[4-(2-quinolinylmethyloxy)benzyloxy]benzo(b)thiophen-2-yl) tetrazole.

27. A compound of claim 1 which is N-1H-(5-tetrazolyl)-5[3-(2-quinolinylmethyloxy)benzyloxy]-3-methylbenzo(b)-thiophene-2-carboxamide.

28. A method for the treatment of hypersensitive ailments in humans and mammals comprising administering thereto an effective amount of a compound of the formula according to claim 1.

29. A pharmaceutical composition wherein the active ingredient is a compound according to claim 1 in admixture with a pharmaceutical carrier.

* * * * *